US011395585B2

(12) United States Patent
Inuzuka

(10) Patent No.: US 11,395,585 B2
(45) Date of Patent: Jul. 26, 2022

(54) OPHTHALMOLOGIC APPARATUS

(71) Applicant: TOPCON CORPORATION, Tokyo (JP)

(72) Inventor: Naoki Inuzuka, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 567 days.

(21) Appl. No.: 16/354,643

(22) Filed: Mar. 15, 2019

(65) Prior Publication Data
US 2019/0290115 A1 Sep. 26, 2019

(30) Foreign Application Priority Data

Mar. 22, 2018 (JP) .......................... JP2018-0054312

(51) Int. Cl.
*A61B 3/00* (2006.01)
*A61B 3/14* (2006.01)
(52) U.S. Cl.
CPC ............ *A61B 3/005* (2013.01); *A61B 3/0033* (2013.01); *A61B 3/0075* (2013.01); *A61B 3/14* (2013.01)
(58) Field of Classification Search
CPC ......... A61B 3/005; A61B 3/0033; A61B 3/14; A61B 3/0075; A61B 3/0083; A61B 3/152; A61B 3/12; G03B 17/48
(Continued)

(56) References Cited

U.S. PATENT DOCUMENTS

2009/0216092 A1* 8/2009 Waldorf .................. A61B 5/16
600/301
2012/0220850 A1* 8/2012 Umekawa .............. A61B 3/165
600/401
(Continued)

FOREIGN PATENT DOCUMENTS

JP 2005-137662 6/2005
JP 2007-44353 2/2007
(Continued)

OTHER PUBLICATIONS

Office Action dated Dec. 7, 2021 in corresponding Japanese Application No. 2018-054312, with Machine-generated English Translation, 4 pages.
(Continued)

*Primary Examiner* — Stephone B Allen
*Assistant Examiner* — Rahman Abdur
(74) *Attorney, Agent, or Firm* — Wenderoth, Lind & Ponack, L.L.P.

(57) ABSTRACT

An ophthalmologic apparatus includes an input portion configured to receive an ID that identifies at least one of an examiner or a subject; a storage portion configured to store examiner data with regard to a rotational position of a supporting arm member (support portion) about a vertical axis and a horizontal axis, the examiner data being predetermined to correspond to the ID; and a drive control portion configured to select the examiner data stored in the storage portion based on the ID received by the input portion, and to control a drive portion based on the examiner data and a detection result of the position detection portion so that the rotational position of the supporting arm member about the vertical axis and the horizontal axis coincides with a predetermined rotational position.

7 Claims, 15 Drawing Sheets

(58) Field of Classification Search
USPC .......................................................... 351/205
See application file for complete search history.

(56) References Cited

U.S. PATENT DOCUMENTS

2013/0293837 A1* 11/2013 Akiba .................... A61B 3/165
351/205
2014/0334075 A1  11/2014 Yamada

FOREIGN PATENT DOCUMENTS

| JP | 2012-148030 | 8/2012 | | |
|----|----|----|----|----|
| JP | 2012-187399 | 10/2012 | | |
| JP | 2019063238 A | * | 4/2019 | ............. A61B 3/113 |

OTHER PUBLICATIONS

Decision to Grant dated Apr. 19, 2022 in corresponding Japanese Patent Application No. 2018-054312, with English translation, 3 pages.

* cited by examiner

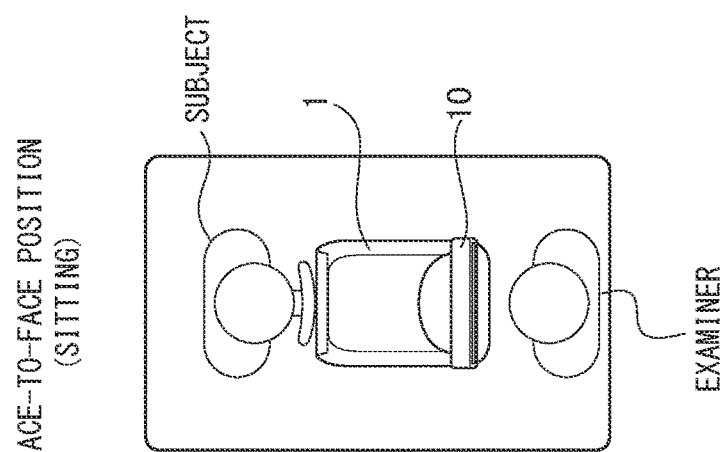
FIG.15A SIDE POSITION
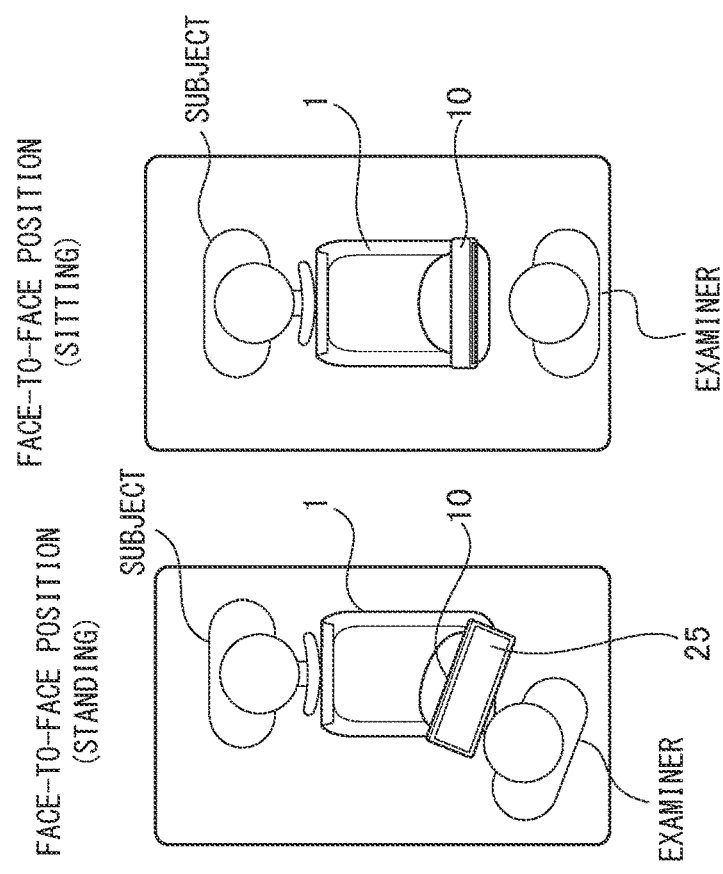
FIG.15B BACK POSITION
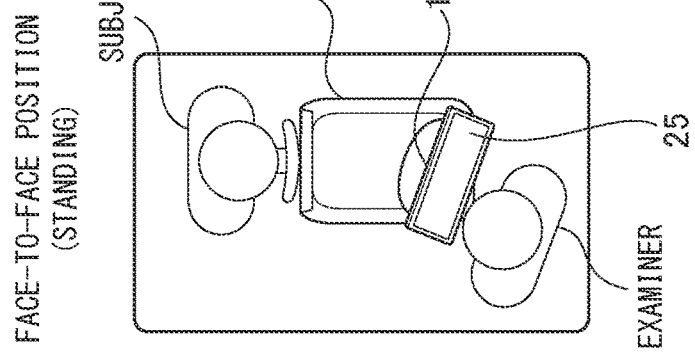
FIG.15C FACE-TO-FACE POSITION (STANDING)
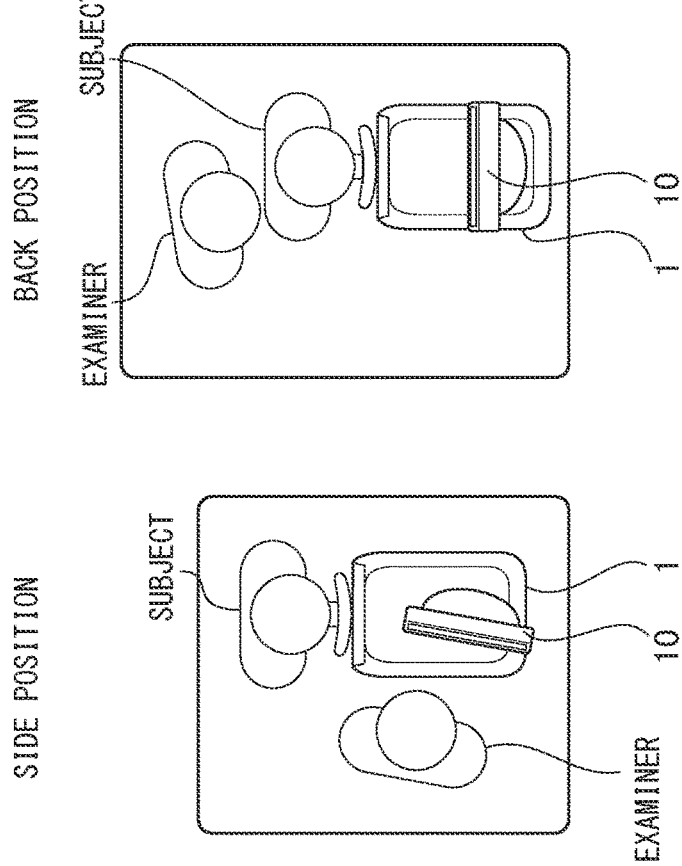
FIG.15D FACE-TO-FACE POSITION (SITTING)

OPHTHALMOLOGIC APPARATUS

CROSS-REFERENCE TO RELATED APPLICATION

This application is based upon and claims the benefit of priority from Japanese Patent Application No. 2018-054312 filed to the Japan Patent Office on Mar. 22, 2018, the entire disclosure of which is incorporated herein by reference.

FIELD OF THE INVENTION

The present disclosure relates to an ophthalmologic apparatus including a monitor which is rotatable about a vertical axis and a horizontal axis.

BACKGROUND

It is known that an ophthalmologic apparatus including a measurement head, a monitor, and a mounting portion (see Patent Literature 1: JP2012-148030A, for example). The measurement head is configured to move in a up and down direction, a left and right direction, and a front and back direction while facing a subject, and to observe and examine a subject eye image via an optical system. The monitor includes a touch panel type display surface which displays at least the subject eye image and operation buttons. The monitor is attached to the mounting portion. The mounting portion is attached to an upper portion of the measurement head. The mounting portion includes a vertical axis portion which rotates about a vertical axis and a horizontal axis portion which rotates about a horizontal axis.

However, the ophthalmologic apparatus disclosed in Patent Literature 1 has following issues since the ophthalmologic apparatus is configured so that an examiner has to manually rotate the monitor about the vertical axis and the horizontal axis.

There are a variety of subjects or patients ranging from infants to the old. For example, the body size of each subject is different from others, or some may have ptosis (dropping eyelids), an eye disease or mental disorder. Accordingly, a wide variety of supports for the subjects are required during the examination by the ophthalmologic apparatus. Accordingly, it may be necessary for the examiner to perform various operations during the examination by the ophthalmologic apparatus. For example, the examiner may have to support the back or the head of the subject so as not to move during the examination, or keep the eyelid of the subject open so that the eyelid does not drop during the examination. Accordingly, it is troublesome that the examiner has to adjust the position or direction of the display surface in the monitor every time the subject changes.

In particular, the examiner often presses buttons with both hands while watching the display surface, and the examiner's hand is often used to hold a written material, a document, an instrument or a terminals. Accordingly, it is troublesome that the examiner has to change the hand holding the document or the like to the other hand, change the position of the display surface and then press the operation buttons.

The body size, the dominant arm, the preferred operational position, and the like are different for each of the examiners. Accordingly, it is troublesome that the examiner has to adjust the position of the display surface in the monitor every time the examiner changes.

Further, the standing position of the examiner may differ depending on the installation location of the ophthalmologic apparatus. Accordingly, it is troublesome that the examiner may have to adjust the position of the display surface every time the ophthalmologic apparatus is moved.

Moreover, it is troublesome that the examiner may have to manually adjust the position or direction of the display surface every time the examiner or the subject changes.

The present disclosure has been made in accordance with the above circumstances, and an object of the present disclosure is to provide an ophthalmologic apparatus which simplifies the adjustment of the position and/or the direction of the display surface in the monitor.

SUMMARY OF THE INVENTION

To achieve the above object, an ophthalmologic apparatus according to the present disclosure may include a base, a measurement head supported by the base to move in a horizontal direction and a vertical direction perpendicular to the horizontal direction while facing a subject in front of the base, the measurement head configured to observe and examine a subject eye image via an optical system;

a monitor including a display surface configured to display at least the subject eye image and an operation button image;

a mounting portion disposed in an upper portion of the measurement head and including a support portion configured to rotatably support the monitor about a vertical axis and a horizontal axis, the monitor attached to the mounting portion;

a drive portion configured to rotate the support portion about the vertical axis and the horizontal axis;

a detection portion configured to detect a rotational position of the support portion about the vertical axis and the horizontal axis;

an input portion configured to receive an input with regard to information that identifies at least one of an examiner or the subject;

a storage portion configured to store data with regard to the rotational position of the support portion about the vertical axis and the horizontal axis, the data being predetermined to correspond to the information; and a drive control portion configured to select the data stored in the storage portion based on the information received by the input portion, and to control the drive portion based on the selected data and a detection result of the detection portion so that the rotational position of the support portion about the vertical axis and the horizontal axis coincides with a predetermined rotational position.

The data may be a rotational position of the support portion about the vertical axis and the horizontal axis detected by the detection portion when at least one of the examiner or the subject in relation to the ophthalmologic apparatus rotates the support portion about the vertical axis and the horizontal axis.

The data may be updated every time the ophthalmologic apparatus is placed on a different installation location.

Further, the data may be updated by data with regard to the rotational position of the support portion about the vertical axis and the horizontal axis detected by the detection portion in a condition where the drive portion is controlled by the drive control portion.

Moreover, the ophthalmologic apparatus may include an authentication portion configured to detect that at least one of the examiner or the subject in relation to the ophthalmologic apparatus approaches the ophthalmologic apparatus and then to authenticate the at least one of the examiner or the subject to output information with regard to the at least one of the examiner or the subject. The drive control portion may be configured to select data stored in the storage portion based on the information output from the authentication portion, and to control the drive portion based on the selected data and a detection result of the detection portion so that the rotational position of the support portion about the vertical axis and the horizontal axis coincides with the predetermined rotational position.

In the ophthalmologic apparatus of the present disclosure as configured above, the drive control portion selects the data stored in the storage portion based on the information received by the input portion, and controls the drive portion based on the selected data and the detection result of the detection portion so that the rotational position of the support portion about the vertical axis and the horizontal axis coincides with a predetermined rotational position.

The drive control portion controls the drive portion so that the rotational position of the support portion about the vertical axis and the horizontal axis coincides with the predetermined rotational position when the information is input via the input portion. Accordingly, the examiner does not need to manually adjust the position of the monitor and/or the direction of the display surface, and the position of the monitor and the direction of the display surface can be controlled and adjusted by the drive control portion. As a result, it is possible to simplify the operation to adjust the direction and/or the position of the display surface in the monitor.

The data stored in the storage portion is a rotational position of the support portion about the vertical axis and the horizontal axis detected by the detection portion when at least one of the examiner or the subject in relation to the ophthalmologic apparatus rotates the support portion about the vertical axis and the horizontal axis. Accordingly, the data can be created by at least one of the examiner or the subject rotating or moving the monitor. As a result, at least one of the examiner or the subject can adjust the position and/or direction of the display surface in the monitor to his or her preferred position and/or direction with a simple operation.

In addition, the data stored in the storage portion is updated every time the ophthalmologic apparatus is placed on a different installation location. Accordingly, the position and/or direction of the display surface in the monitor can be adjusted based on the installation location of the ophthalmologic apparatus.

Further, the data stored in the storage portion is updated by data with regard to the rotational position of the support portion about the vertical axis and the horizontal axis detected by the detection portion in a condition where the drive portion is controlled by the drive control portion. Accordingly, when at least one of the examiner or the subject finely or slightly adjusts the rotational position of the monitor, the finely adjusted rotational position becomes a next drive target for the drive control portion. As a result, the position and/or direction of the display surface in the monitor can always be adjusted appropriately.

Moreover, the drive control portion is configured to select the data stored in the storage portion based on the information output from the authentication portion, and to control the drive portion based on the selected data and the detection result of the detection portion so that the rotational position of the support portion about the vertical axis and the horizontal axis coincides with the predetermined rotational position. Accordingly, the position and/or direction of the display surface in the monitor can be adjusted when the examiner or the subject approaches the ophthalmologic apparatus. As a result, it is possible to further simplify the operation to adjust the direction and/or the position of the display surface in the monitor.

BRIEF DESCRIPTION OF THE DRAWINGS

FIG. 1A shows a side view, and FIG. 1B shows a front view.

FIG. 2A shows a side view, and FIG. 2B shows a back view.

FIG. 3A shows a side view, and FIG. 3B shows a back view.

FIG. 4A shows a side view, and FIG. 4B shows a back view.

FIG. 5A shows a side view, and FIG. 5B shows a back view.

FIGS. 15A to 15D are views illustrating an example of the positional relation among an examiner, a subject, and a display surface of a monitor in the ophthalmologic apparatus according to the embodiment of the present disclosure.

DETAILED DESCRIPTION

Hereinafter, an embodiment of the present disclosure will be described with reference to the drawings. FIGS. 1A to 5B illustrate a front view, a side view and a back view each illustrate an ophthalmologic apparatus according to an embodiment of the present disclosure.

Each drawings includes a X-axis, a Y-axis and a Z-axis, and the present disclosure will be described based on left and right directions (a X-axis positive direction corresponds to a left direction, and a X-axis negative direction corresponds to a right direction), front and back directions (a Y-axis positive direction corresponds to a back direction, and a Y-axis negative direction corresponds to a front direction), and upward and downward directions (a Z-axis positive direction corresponds to an upward direction, and a Z-axis negative direction corresponds to a downward direction) in FIG. 1B. In addition, a horizontal direction is a direction along an X-Y plane, and a vertical direction is a direction along the Z-axis.

Figure 1A:
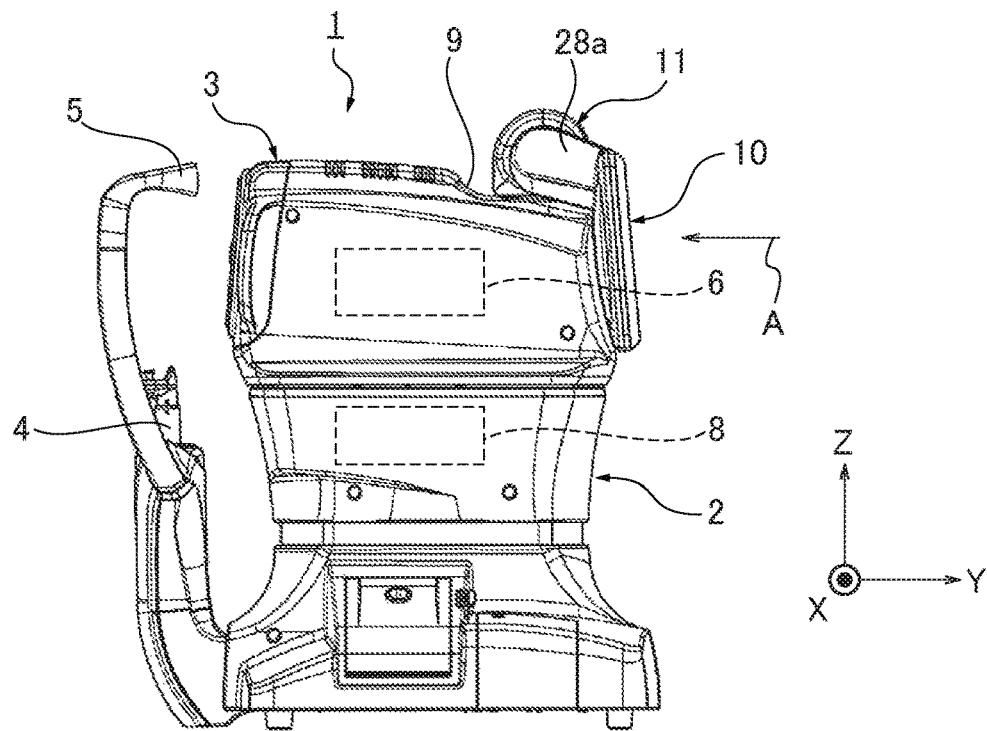
FIGS. 1A, 1B illustrate an ophthalmologic apparatus according to an embodiment of the present disclosure.
Figure 1B:
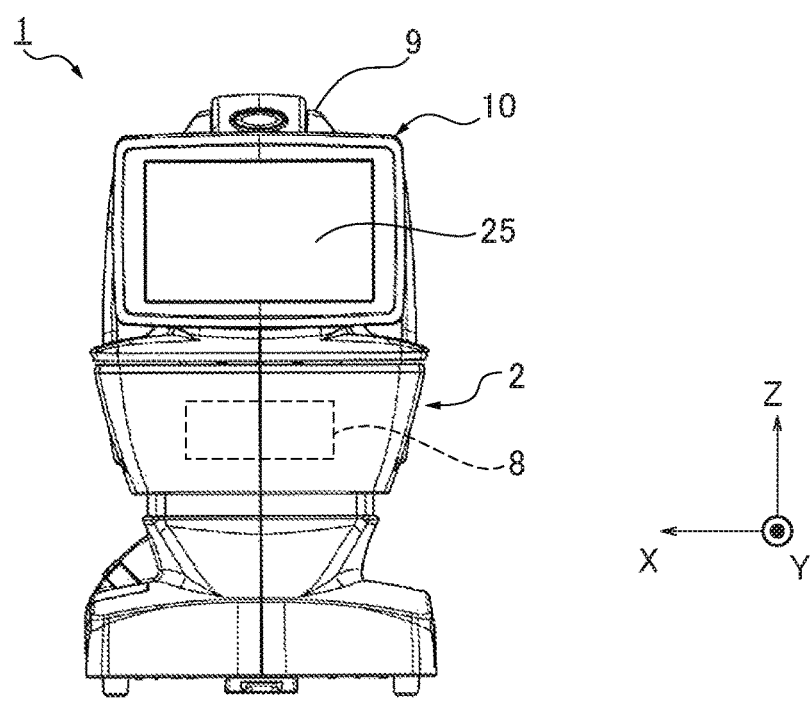

More specifically, FIGS. 1A, 1B are views illustrating the position of a monitor when an examiner faces a patient or subject with the ophthalmologic apparatus therebetween and performs an examination. FIG. 1A is a side view illustrating a condition in which a display surface of the monitor faces the examiner, and FIG. 1B is a front view illustrating the display surface of the monitor seen from a direction shown with an arrow A in FIG. 1A.

Figure 2A:
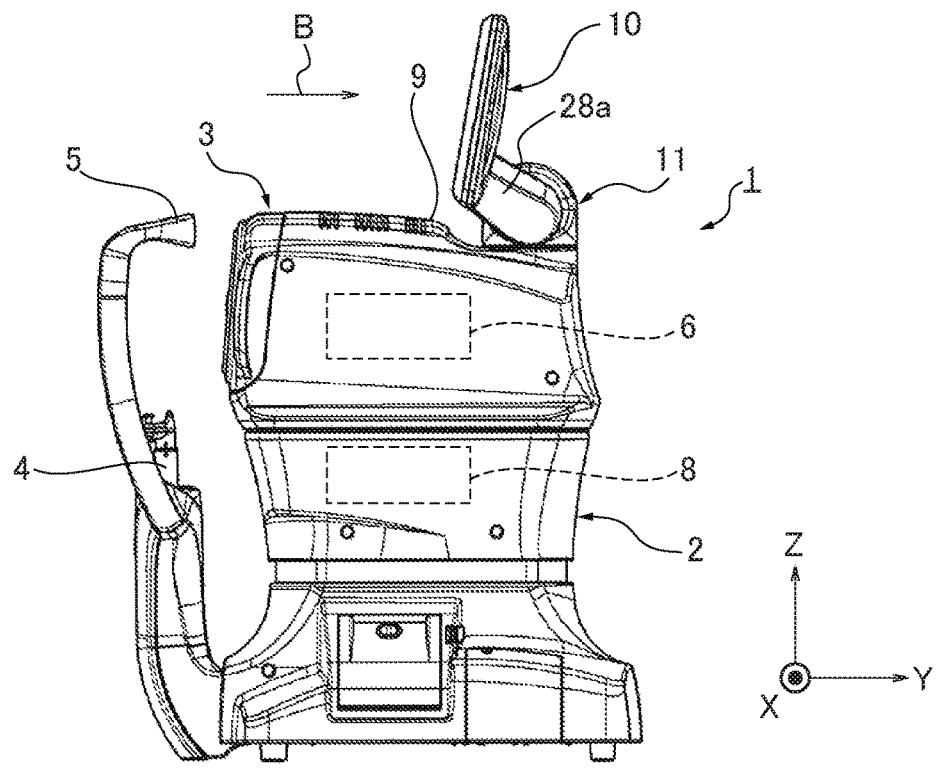
FIGS. 2A, 2B illustrate the ophthalmologic apparatus according to the embodiment of the present disclosure.
Figure 2B:
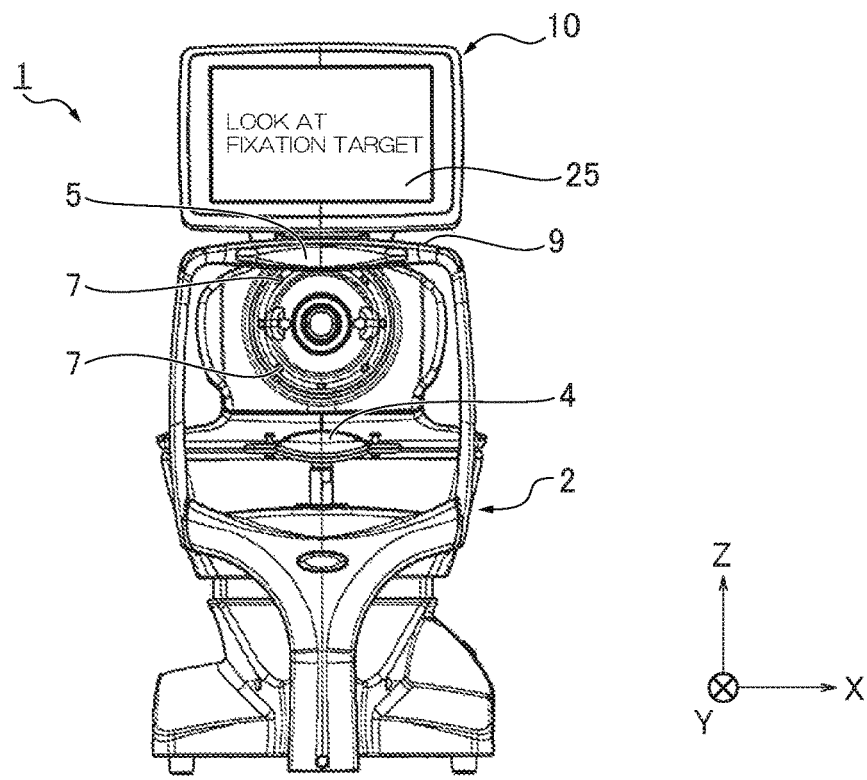

FIGS. 2A, 2B are views illustrating the position of the monitor when the examiner stands on the same side as the subject to perform the examination. FIG. 2A is a side view illustrating a condition in which the display surface of the monitor faces the subject, and FIG. 2B is a back view illustrating the display surface of the monitor seen from a direction shown with an arrow B in FIG. 2A.

Figure 3A:
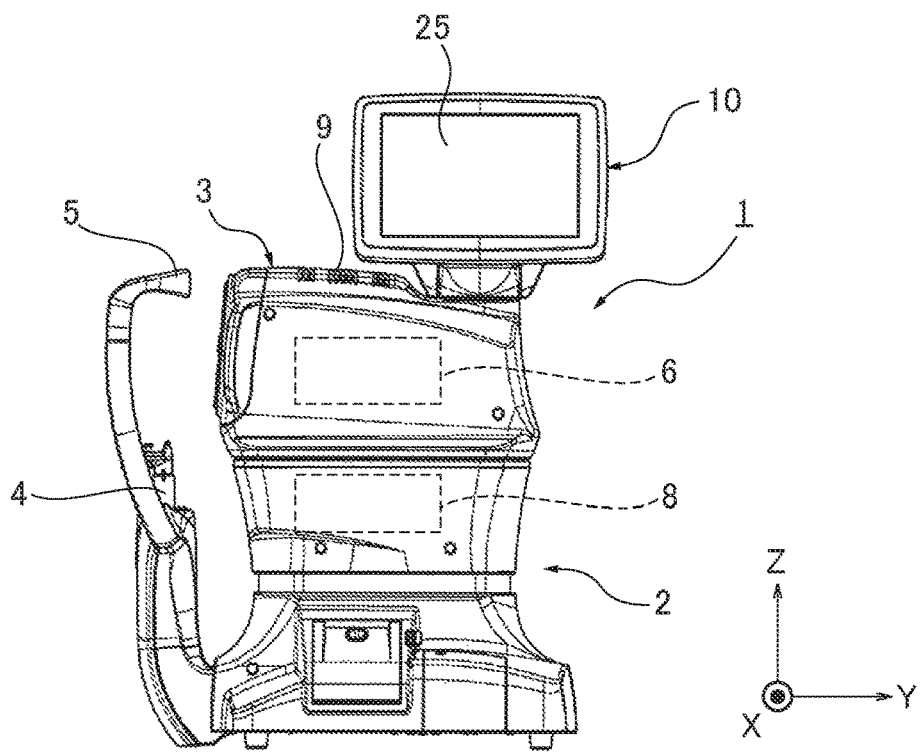
FIGS. 3A, 3B illustrate the ophthalmologic apparatus according to the embodiment of the present disclosure.
Figure 3B:
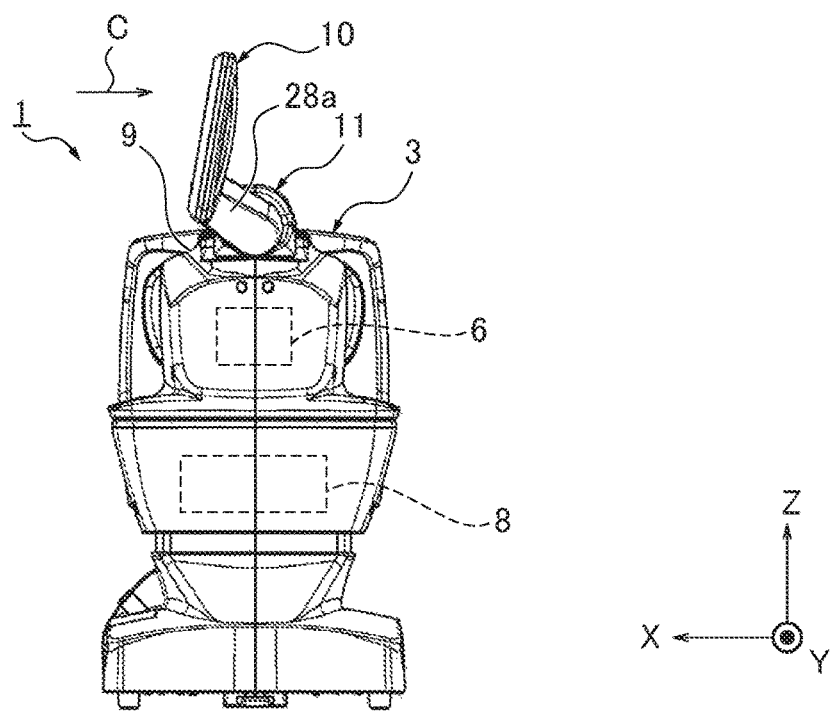

FIGS. 3A, 3B are views illustrating the position of the monitor when the examiner stands on the right side of the ophthalmologic apparatus to perform the examination. FIG. 3A is a side view of the ophthalmologic apparatus illustrating the display surface of the monitor seen from a direction shown with an arrow C in FIG. 3B, and FIG. 3B is a back view illustrating a condition in which the display surface of the monitor faces the right side of the subject.

Figure 4A:
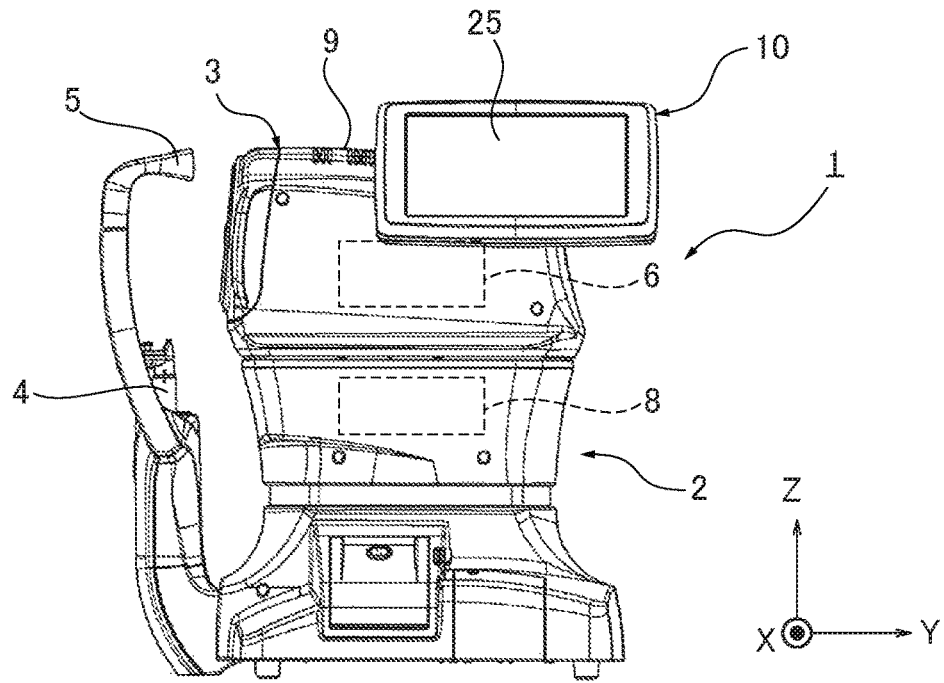
FIGS. 4A, 4B illustrate the ophthalmologic apparatus according to the embodiment of the present disclosure.
Figure 4B:
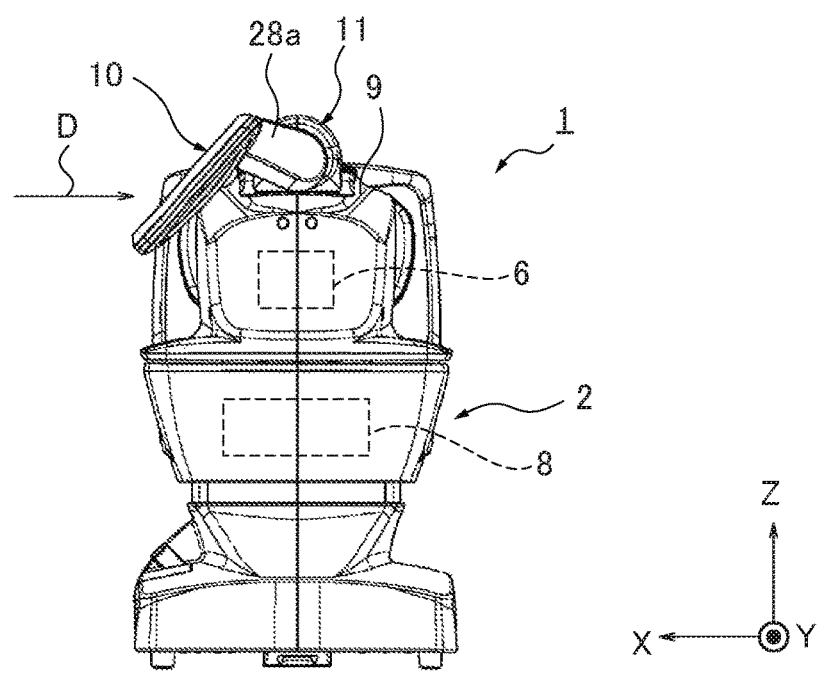

FIGS. 4A, 4B are views illustrating the position of the monitor when the examiner is seated on the right side of the ophthalmologic apparatus to perform the examination. FIG. 4A is a side view illustrating the display surface of the monitor seen from a direction shown with an arrow D in FIG. 4B, and FIG. 4B is a back view illustrating a condition in which the display surface of the monitor faces the right side of the subject.

Figure 5A:
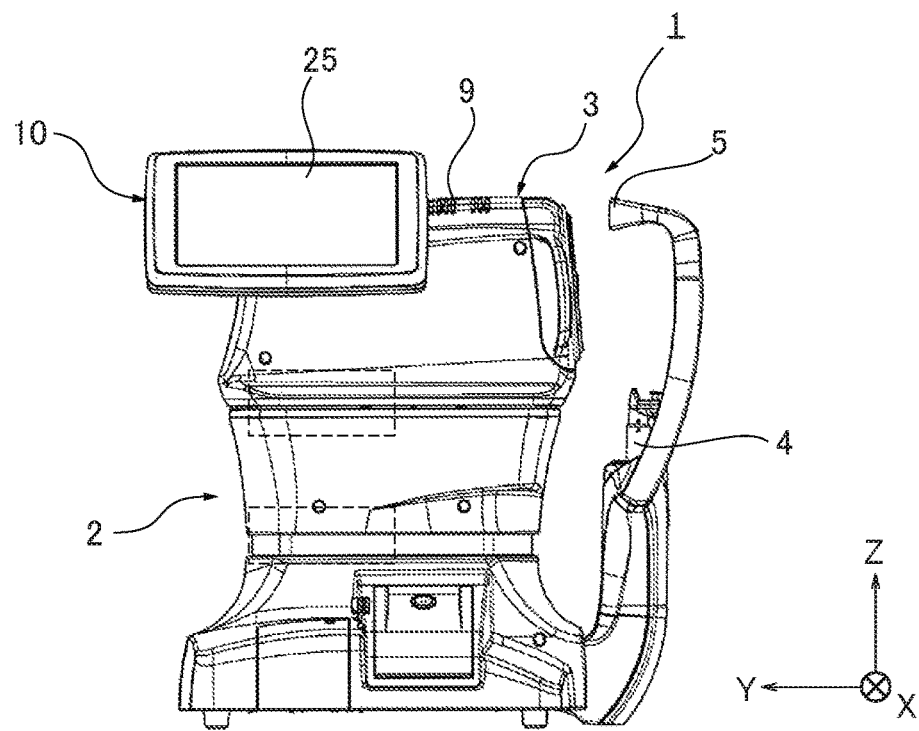
FIGS. 5A, 5B illustrate the ophthalmologic apparatus according to the embodiment of the present disclosure.
Figure 5B:
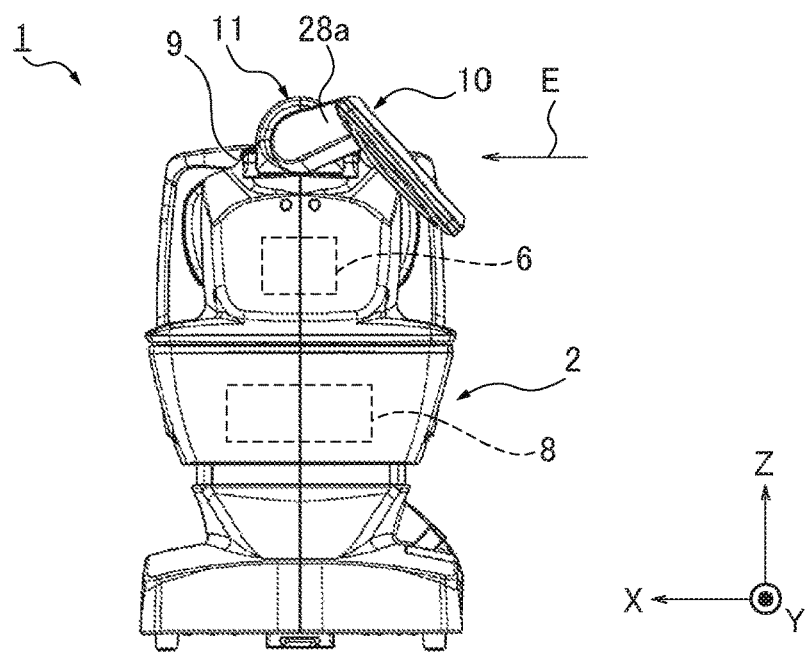

FIGS. 5A, 5B are views illustrating the position of a monitor when the examiner is seated on the left side of the ophthalmologic apparatus to perform the examination. FIG. 5A is a side view illustrating the display surface of the monitor seen from a direction shown with an arrow E in FIG. 5B, and FIG. 5B is a back view illustrating a condition in which the display surface of the monitor faces the left side of the subject.

An ophthalmologic apparatus 1 according to an embodiment of the present disclosure includes a base 2 and a measurement head 3. A jaw rest 4 is disposed in front of the base 2. A forehead rest 5 is integrally formed with the jaw rest 4 and disposed above the jaw rest 4. A chair or the like is placed in front of the ophthalmologic apparatus 1. The subject sits on the chair or the like to face the ophthalmologic apparatus 1, puts his or her jaw on the jaw rest 4, puts his or her forehead on the forehead rest 5 and undergoes an examination.

As shown with a dashed line in FIGS. 1A to 5B, a known optical system 6 for observation/photography is disposed within the measurement head 3. The optical system 6 observes and photographs the anterior ocular segment, the cornea, the ocular fundus and the like of the subject As shown with a dashed line in FIGS. 1A to 5B, the base 2 includes a known drive mechanism/drive circuit 8 for driving the measurement head 3. For example, a stepping motor (not shown) is used as a drive portion of the drive mechanism/drive circuit 8.

By operating a touch panel type display surface 25 of a monitor 10, the drive mechanism/drive circuit 8 drives the measurement head 3 to move in the horizontal direction and the vertical direction perpendicular to the horizontal direction relative to the base 2. In other words, the measurement head 3 is movably supported by the base 2 in the horizontal direction and the vertical direction.

A mounting portion 11 is disposed in an upper portion 9 of the measurement head 3, and the monitor 10 is attached to the mounting portion 11. The monitor 10 includes the display surface 25 which displays at least subject eye images and operation button images.

Figure 6:
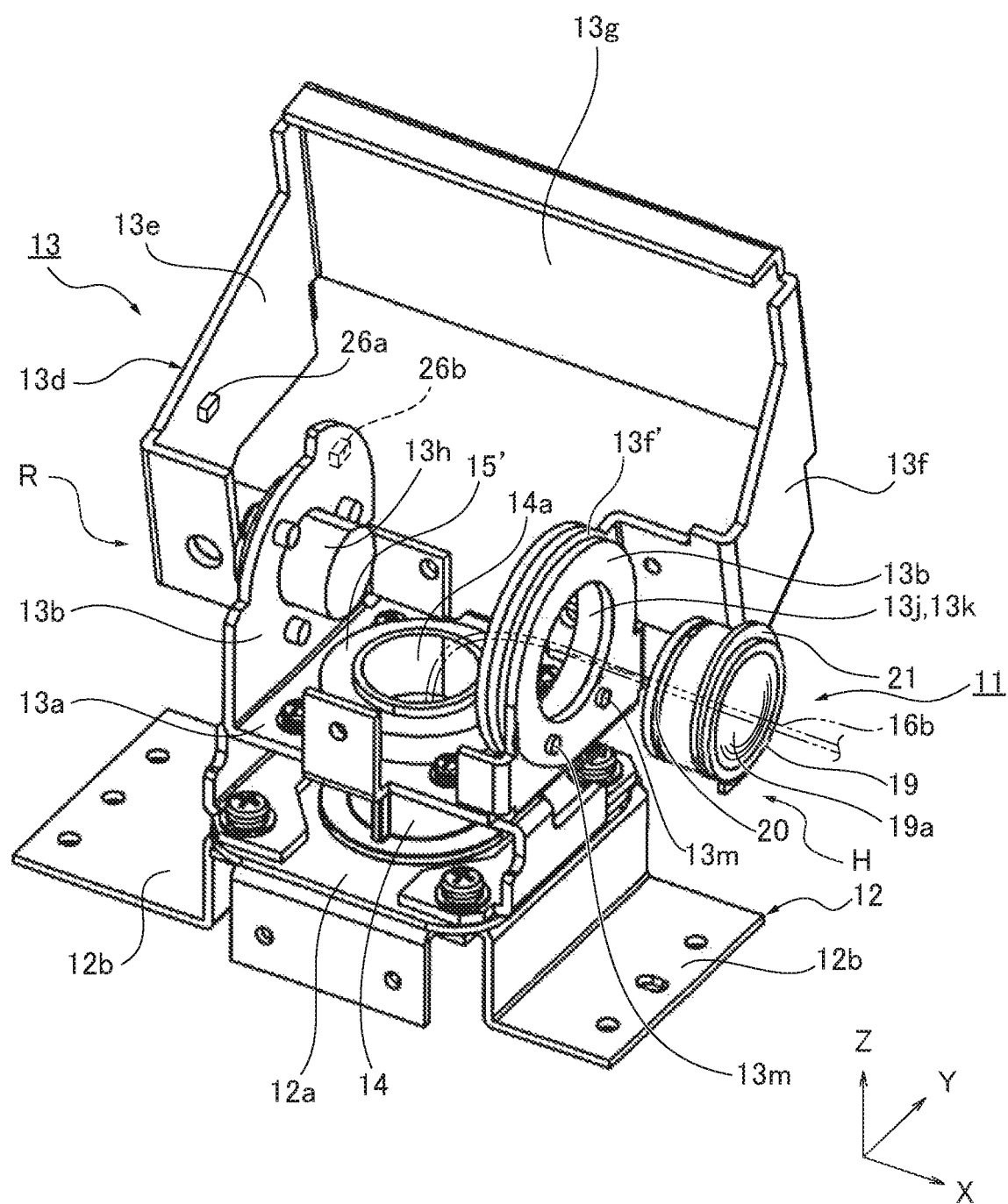
FIG. 6 is a perspective view illustrating the configuration of a mounting portion in the ophthalmologic apparatus according to the embodiment of the present disclosure.

The detailed configuration of the mounting portion 11 will be described with reference to FIG. 6 and other drawings. As shown in FIG. 6, the mounting portion 11 includes a fixed portion R which is fixed to the upper portion 9 (now shown in FIG. 6) of the measurement head 3. The fixed portion R includes a vertical axis receiving member 12 made of sheet metal, and a horizontal axis receiving member 13 made of sheet metal.

The vertical axis receiving member 12 includes a seat 12a and a pair of fixed plate members 12b. The seat 12a is a flat plate. The fixed plate members 12b are disposed on the right and left sides of the seat 12a, and extend from the seat 12a in the right and left directions of the seat 12a.

The fixed plate members 12b are fixed to the upper portion 9 of the measurement head 3 with fixing members such as a screw (now shown). A vertical tube 14 is welded and fixed to a substantially central portion of the seat 12a by welding means, for example. The longitudinal direction of the vertical tube 14 extends in the vertical direction.

Figure 7:
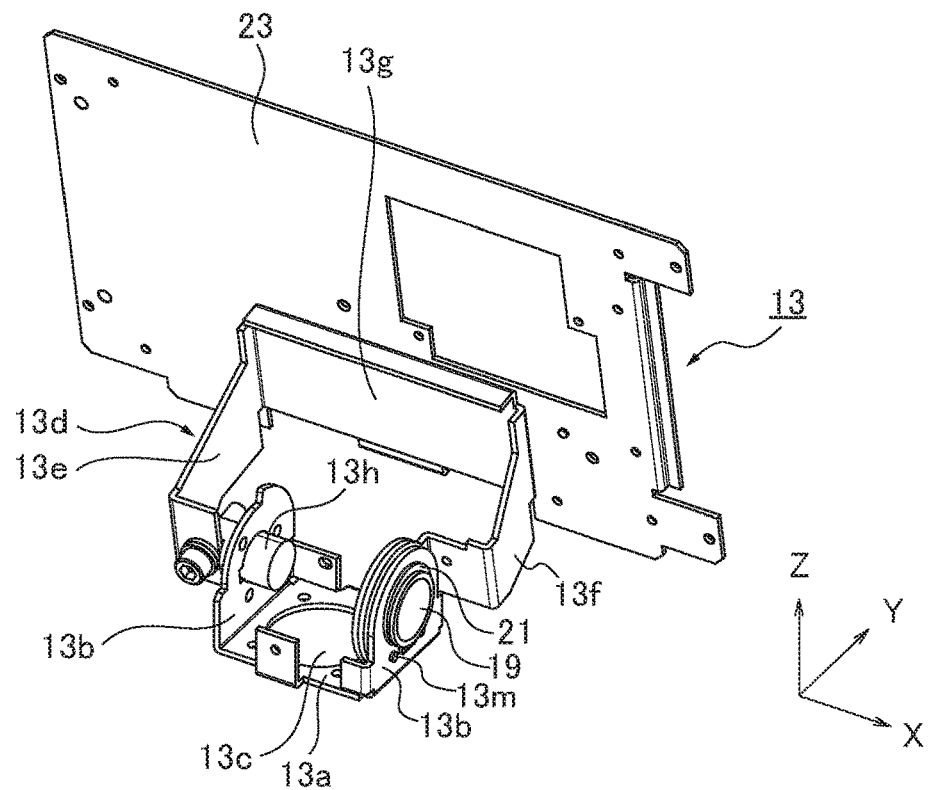
FIG. 7 is a partial exploded perspective view illustrating the positional relation between the mounting portion and a circuit board of the ophthalmologic apparatus according to the embodiment of the present disclosure.

As shown in FIGS. 6 and 7, the horizontal axis receiving member 13 includes a horizontal plate member 13a, and a pair of the supporting plate members 13b. The supporting plate members 13b are disposed on the right and left ends of the horizontal plate member 13a and extend upward in the figure.

As shown in FIG. 7, a circular opening 13c is formed in a substantially central portion of the horizontal plate member 13a. The vertical tube 14 extends through the circular opening 13c.

Figure 8:
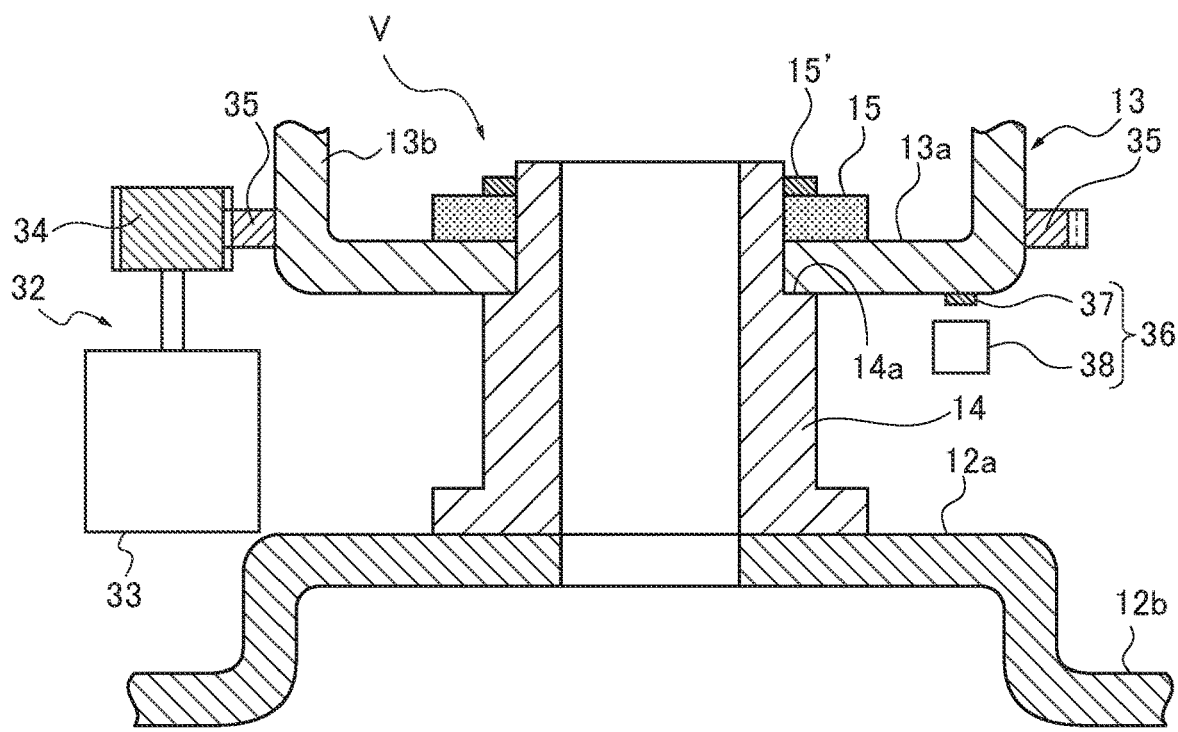
FIG. 8 is a partial cross-sectional view illustrating the mounting structure of a vertical tube of the mounting portion in the ophthalmologic apparatus according to the embodiment of the present disclosure.

As shown in FIG. 8, a step portion 14a having a smaller diameter is formed on the upper end of the vertical tube 14. The step portion 14a of the vertical tube 14 is inserted into a friction ring plate 15 to hold the horizontal plate member 13a of the horizontal axis receiving member 13 between the friction ring plate 15 and the vertical tube 14 from above and below in the figure. In addition, the step portion 14a is inserted into a retaining ring 15' to hold the friction ring plate 15 and the horizontal plate member 13a between the retaining ring 15' and the vertical tube 14. Each of the friction ring plate 15 and the retaining ring 15' has a disc shape. The diameter of the retaining ring 15' is smaller than that of the friction ring plate 15.

Accordingly, the horizontal plate member 13a is supported around the step portion 14a of the vertical tube 14 with appropriate downward pressure by the retaining ring 15' and the friction ring plate 15 in the vertical axis direction so that the horizontal plate member 13a can rotate about the axis of the vertical tube 14, more specifically, about the rotational axis along the Z-axis direction and can keep staying at appropriate positions around the vertical axis (the Z-axis).

As shown in FIGS. 6 and 7, a supporting arm 13*d* is attached to the pair of the supporting plate members 13*b*, 13*b*. The supporting arm 13*d* configures a support portion of the present disclosure. The supporting arm 13*d* includes a pair of arm plate members 13*e*, 13*f*, and a mounting bracket plate 13*g* disposed between distal ends of the arm plate members 13*e*, 13*f*.

The arm plate member 13*e* is located on the upper left side in FIGS. 6 and 7 and the arm plate member 13*f* is located on the bottom right in FIGS. 6 and 7. The arm plate member 13*e* includes a horizontal axis supporting portion 13*h* and the arm plate member 13*f* includes a circular opening 13*j*.

The horizontal axis supporting portion 13*h* is supported by one of the supporting plate members 13*b*, i.e. the supporting plate member 13*b* located on the upper left in FIGS. 6 and 7 so as to rotate about the horizontal axis, more specifically, about the rotational axis along the X-axis direction. A known torque hinge is used for the horizontal axis supporting portion 13*h*. The torque hinge makes it possible to adjust the turning force about the horizontal axis.

Figure 9:
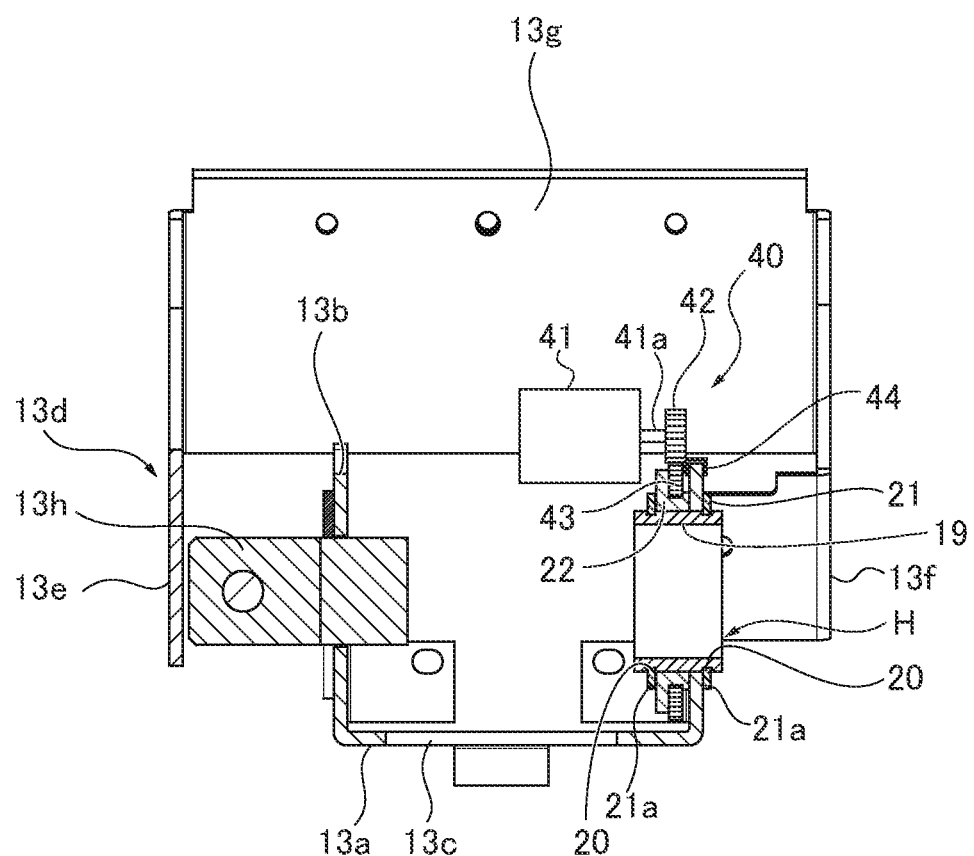
FIG. 9 is a cross-sectional view illustrating the mounting structure of a hollow tube of the mounting portion in the ophthalmologic apparatus according to the embodiment of the present disclosure.

The other of the supporting plate members 13*b*, i.e. the supporting plate member 13*b* located on the bottom right in FIGS. 6 and 7 includes a circular opening 13*k* at a location facing the circular opening 13*j*. The circular opening 13*k* has a diameter substantially same as that of the circular opening 13*j*. As shown in FIGS. 6, 7 and 9, a hollow tube 19 is inserted into the circular openings 13*j*, 13*k* and fixed to the other supporting plate member 13*b*.

The hollow tube 19 and the horizontal axis supporting portion 13*h* allow the supporting arm 13*d* to rotate about the horizontal axis, more specifically, about the rotational axis along the X-axis direction. Accordingly, the hollow tube 19 and the horizontal axis supporting portion 13*h* form a horizontal axis portion H according to the embodiment of the present disclosure. On the other hand, the vertical tube 14, the friction ring plate 15 and the retaining ring 15' allow the horizontal axis receiving member 13 which supports the supporting arm 13*d* to rotate about the vertical axis, more specifically, about the rotational axis along the Z-axis direction. Accordingly, the vertical tube 14, the friction ring plate 15 and the retaining ring 15' form a vertical axis portion V according to the embodiment of the present disclosure.

As shown in FIG. 8 in detail, the vertical axis portion V is attached to a vertical rotary drive 32. The vertical rotary drive 32 drives the horizontal axis receiving member 13, more specifically, the supporting plate members 13*b* to rotate about the vertical axis, more specifically, about the rotational axis along the Z-axis direction. The vertical rotary drive 32 includes a DC motor 33, a gear 34, and a ring gear 35. The DC motor 33 is supported between the vertical axis receiving member 12 and the horizontal axis receiving member 13 by a support mechanism (now shown). The gear 34 is attached to the distal end of an output shaft 33*a* of the DC motor 33. The ring gear 35 is disposed concentrically with the circular opening 13*c* in the bottom side of the supporting plate members 13*b* of the horizontal axis receiving member 13. The ring gear 35 meshes with the gear 34.

Accordingly, when the drive power is supplied to the DC motor 33 of the vertical rotary drive 32, the output shaft 33*a* of the DC motor 33 is rotationally driven. The rotation of the output shaft 33*a* rotationally drives the gears 34, 35 and accordingly the horizontal axis receiving member 13 is driven to rotate about the vertical axis.

Further, the vertical axis portion V is provided with a vertical rotational position detector 36 which detects the rotational position of the horizontal axis receiving member 13. The vertical rotational position detector 36 includes a ring shaped detection plate 37 and a detection sensor 38. The detection plate 37 is disposed on the bottom surface of the supporting plate members 13*b*. The detection sensor 38 is disposed at a position facing the detection plate 37 and detects the moving distance of the detection plate 37. For example, the detection plate 37 is a plate on which a black and white pattern is periodically drawn, and the detection sensor 38 is an optical sensor for detecting the intensity of the reflected light from the detection plate 37.

As shown in FIG. 9 in detail, the horizontal axis portion H includes a horizontal rotary drive 40 which rotationally drives the supporting arm 13*d* about the horizontal axis, more specifically, about the rotational axis along the X-axis direction. The horizontal rotary drive 40 includes a DC motor 41, a gear 42 and a gear 43. The DC motor 41 is supported between the pair of arm plate members 13*e*, 13*f* by a support mechanism (now shown). The gear 42 is attached to the tip of an output shaft 41*a* of the DC motor 41. The gear 43 is disposed concentrically with the supporting plate member 13*b* located on the right side in FIG. 9 to mesh with the gear 42.

Accordingly, when the drive power is supplied to the DC motor 41 of the horizontal rotary drive 40, the output shaft 41*a* of the DC motor 41 is rotationally driven. The rotation of the output shaft 41*a* rotationally drives the gears 42, 43 and accordingly the supporting arm 13*d* is driven to rotate about the horizontal axis.

Further, the horizontal axis portion H includes an encoder 44 which is a horizontal rotational position detector to detect the rotational position of the supporting arm 13*d*.

As shown in FIG. 9, the hollow tube 19 includes a pair of circular grooves 20, 20 which are separated from each other in the axial direction (a longitudinal direction) of the hollow tube 19. C-shaped retaining rings 21, 21 are disposed within the circular grooves 20, 20 as axial retaining rings. This prevents the hollow tube 19 from being disengaged from the supporting plate members 13*b* in the axial direction.

As shown in FIG. 9, a bearing flange 22 made of resin is inserted through the hollow tube 19. The supporting arm 13*d* rotatably and slidingly contacts the bearing flange 22 by receiving an appropriate force.

In FIG. 9, a bended plate 13*f'* is formed in the arm plate member 13*f* and includes the circular opening 13*j*. The hollow tube 19 rotatably supports the arm plate member 13*f* via the bended plate 13*f'*.

Figure 10:
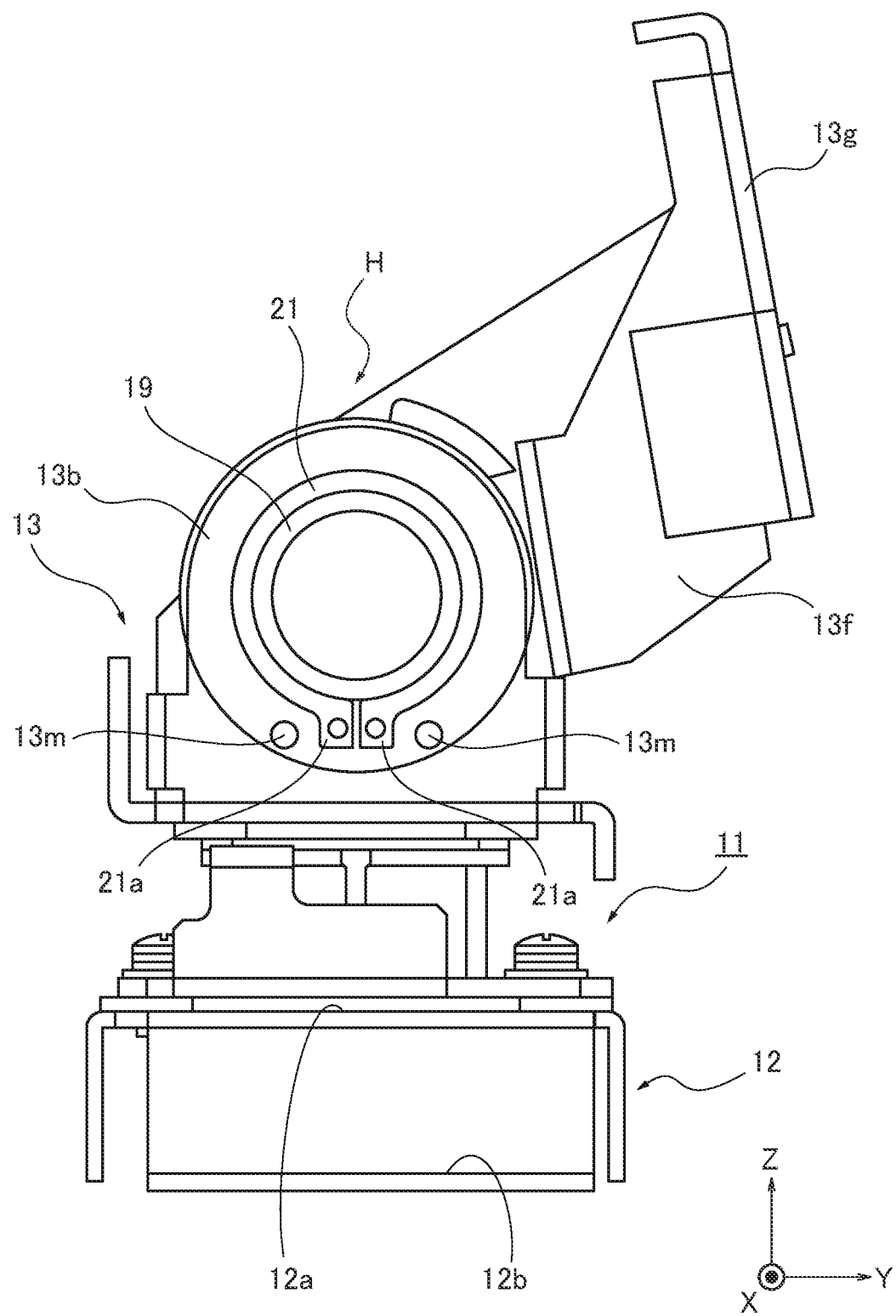
FIG. 10 is a side view illustrating the configuration of the mounting portion in the ophthalmologic apparatus according to the embodiment of the present disclosure.

As shown in FIGS. 6 and 10, the supporting plate member 13*b* which rotatably supports the hollow tube 19 includes a pair of protrusions 13*m*, 13*m*. The protrusions 13*m*, 13*m* are separated from each other around the horizontal axis, more specifically, in the circumferential direction of the supporting plate members 13*b*. As shown in FIG. 10, open ends 21*a*, 21*a* of the C-shaped retaining ring 21 are placed between the protrusions 13*m*, 13*m*.

Placing the open ends 21*a*, 21*a* of the C-shaped retaining ring 21 between the protrusions 13*m*, 13*m* prevents the hollow tube 19 from rotating about the horizontal axis, which improves the durability of the hollow tube 19.

As shown in FIG. 6, a lead wire 16*b* is drawn out of a through hole 19*a* of the hollow tube 19 and a through hole 14*b* of the vertical tube 14. The lead wire 16*b* electrically connects the monitor 10 and the measurement head 3. This prevents the twist of the lead wire 16*b* which may otherwise be caused by the rotational movement of the monitor 10.

As shown in FIGS. 6, 7 and 9, the mounting bracket plate 13g is disposed between the distal ends of the pair of the arm plate members 13e, 13f as described above. As shown in FIG. 7, a circuit board 23 is attached to the mounting bracket plate 13g.

A control circuit unit (now shown) is disposed on the back side of the circuit board 23, and a liquid crystal display (now shown) is disposed on the front side of the control circuit unit substantially parallel to the circuit board 23. As shown in FIGS. 1B, 2B, 3A, 4A and 5A, the liquid crystal display includes the display surface 25.

As specifically shown in FIG. 10, the mounting bracket plate 13g and each of the arm plate members 13e, 13f form an obtuse angle therebetween. More specifically, the shapes of the mounting bracket plate 13g and the arm plate members 13e, 13f are defined so that the normal line of the surface of the mounting bracket plate 13g and the vertical plane (the X-Z plane) through the rotational axis (the X-axis) of the horizontal axis portion H form an obtuse angle therebetween.

The display surface 25 of the liquid crystal display in the monitor 10 is substantially parallel to a (right) surface of the mounting bracket plate 13g, and accordingly, the angle between the monitor 10 and the supporting arm 13d becomes an obtuse angle. Thereby, the monitor 10 can be easily moved from one side facing the examiner to the other side facing the subject.

As shown in FIG. 6, the arm plate member 13e includes a detection sensor 26a and the supporting plate member 13b includes a detection sensor 26b. The detection sensors 26a, 26b detect the rotation of the monitor 10 (the pair of the arm plate members 13e, 13f) about the horizontal axis. For example, the detection sensors 26a, 26b are configured to be turned on when the display surface 25 of the monitor 10 is in the horizontal condition and turned off when the display surface 25 exceeds a predetermined angle from the horizontal condition.

The control circuit unit controls in cooperation with the detection sensors 26a, 26b so that appearance positions of the subject eye image and the operation button images are the same before and after the display surface 25 is turned upside down by rotating the monitor 10 about the horizontal axis, and image information on the display surface 25 flips vertically and horizontally.

For example, the control circuit unit controls so that the image information on the display surface 25 flips vertically and horizontally when the rise and fall of the output signals from the detection sensors 26a, 26b are detected.

Figure 16:
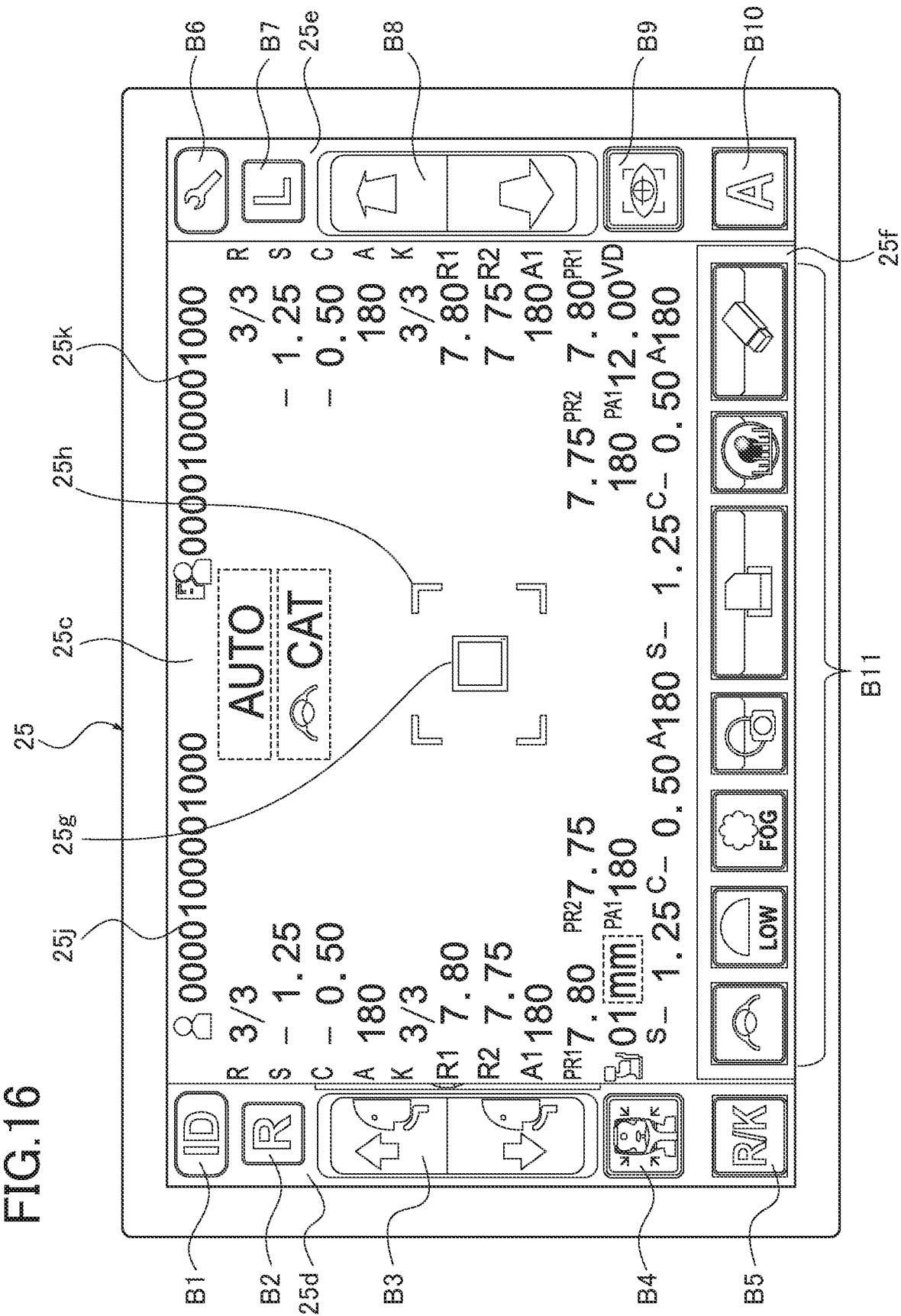
FIG. 16 is a view illustrating an example of operational button images on the display surface of the ophthalmologic apparatus according to the embodiment of the present disclosure.

As shown in the enlarged view of FIG. 16, the display surface 25 is rectangular. The display surface 25 includes a subject eye image display area 25c, and operation button image display areas 25d, 25e and 25f. A rectangular target area mark 25g and a minimum pupil diameter determination mark 25h are displayed on the subject eye image display area 25c. The target area mark 25g is located in the center of the area 25c.

The operation button image display areas 25d and 25e are located along the left and right sides of the display surface 25 respectively with the subject eye image display area 25c located therebetween. The operation button image display area 25f is located along the bottom side of the subject eye image display area 25c.

The display area 25d on the left side of the display surface 25 includes an ID button B1, a R button B2, a jaw rest up and down button B3, a reset button B4, and a measurement mode button B5. The display area 25e on the right side of the display surface 25 includes a setup button B6, an L button B7, a measurement head front and back button (Z direction button) B8, a start button B9, and a manual/auto switching button B10. The measurement head front and back button B8 is used to move the measurement head 3 forward and backward. The display area 25f includes various functional buttons B11 along the bottom side of the display surface 25.

The ID button B1 is used to input the ID of the patient (the subject) and the ID of the examiner. A patient ID display area 25j and an examiner ID display area 25k are placed in the upper portion of the subject eye image display area 25c. The ID of the patient and the ID of the examiner input by the ID button B1 are displayed on the patient ID display area 25j and the examiner ID display area 25k, respectively.

The reset button B4 is used to reset the settings of the entire ophthalmologic apparatus 1. The measurement mode button B5 is used to select a REF (eye refractive power) measurement mode, a KERATO (corneal shape) measurement mode or a REF/KERATO measurement mode. The R button B2 is used to select a right eye, and the L button B7 is used to select a left eye. The start button B9 is used to start the measurement during the manual mode. The setup button B6 is used to display a setup image.

The jaw rest up and down button B3 is used to move the jaw rest 4 upward and downward to adjust the height of the eyes of the subject. The measurement head front and back button (the Z direction button) B8 is used to move the measurement head 3 forward and backward relative to the eyes of the subject.

The minimum pupil diameter determination mark 25h is used to stop the measurement when the pupil diameter is equal to or smaller than the minimum pupil diameter determination mark 25h.

The subject eye image display area 25c displays an image of the anterior segment of the eye under the observation as well as letters, symbols, marks, numbers, images such as diagrams, graphics or the like with regard to the measurement results and/or the examination.

Figure 11:
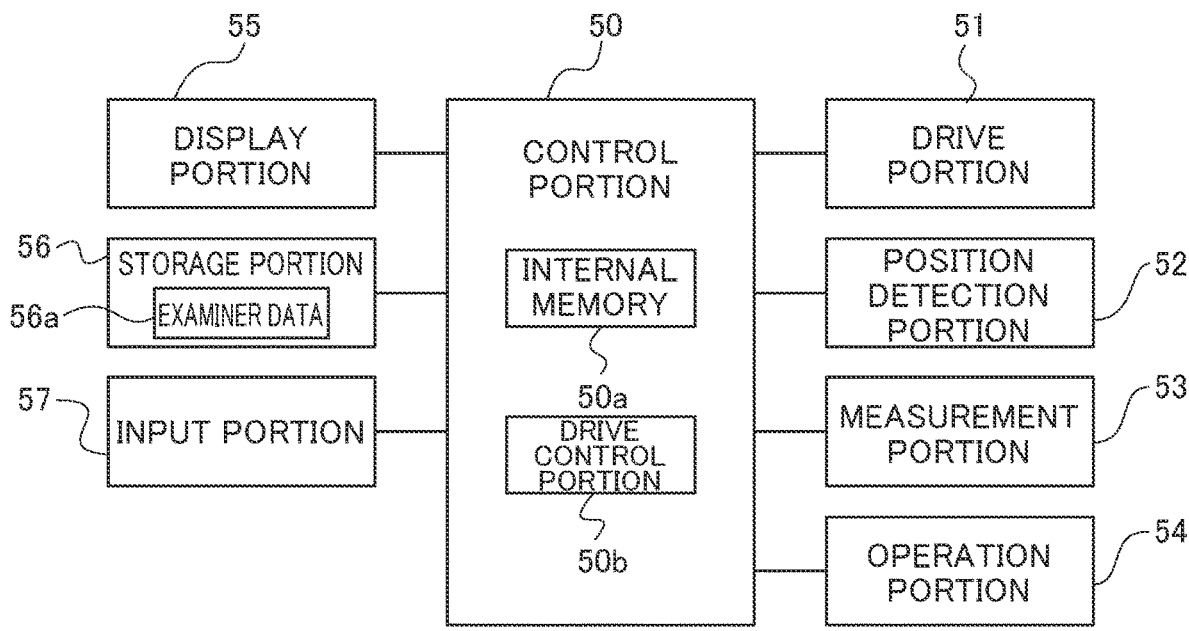
FIG. 11 is a block diagram illustrating the configuration of the ophthalmologic apparatus according to the embodiment of the present disclosure.

Next, the control system of the ophthalmologic apparatus 1 will be described with reference to FIG. 11. The ophthalmologic apparatus 1 according to the embodiment of the present disclosure includes a control portion 50, a drive portion 51, a position detection portion (detection portion) 52, a measurement portion 53, an operation portion 54, a display portion 55, a storage portion 56 and an input portion 57.

The control portion 50 configures an electric control system in the ophthalmologic apparatus 1, and comprehensively controls each portion of the ophthalmologic apparatus 1 according to a program stored in an internal memory 50a.

The control portion 50 appropriately controls the drive portion 51 based on the measurement result from the measurement portion 53 and the operational instruction from the operation portion 54, and adjusts the positions of the measurement head 3 in the horizontal direction and the vertical direction relative to the base 2 while referring to the position detection result by the position detection portion 52. In addition, the control portion 50 appropriately controls the drive portion 51 based on the rotational position detection result of the supporting plate members 13b and the supporting arm 13d from the position detection portion 52, and controls the rotational positions of the supporting plate members 13b and the supporting arm 13d.

Further, the control portion 50 observes and examines the subject eye image by the measurement portion 53 based on the instruction from the operation portion 54, and displays the subject eye image and the examination result on the display surface 25 of the display portion 55 as shown in FIG.

16, for example. In addition, the control portion 50 displays the operation button images on the display surface 25 of the display portion 55 as shown in FIG. 16.

Moreover, the control portion 50 also functions as a drive control portion 50b by the program stored in the internal memory 50a being executed. The drive control portion 50b selects examiner data 56a stored in the storage portion 56 based on information input to the input portion 57. Then, the drive control portion 50b controls the drive portion 51 based on the detection result of the position detection portion 52 and the examiner data 56a such that the rotational position of the supporting arm 13d about the vertical axis and the horizontal axis coincides with a predetermined rotational position. The operation of the drive control portion 50b will be described in detail later.

The drive portion 51 includes the drive mechanism/drive circuit 8 in the base 2, and the vertical rotary drive 32 and the horizontal rotary drive 40 in the mounting portion 11. The vertical rotary drive 32 and the horizontal rotary drive 40 drive the supporting plate members 13b and the supporting arm 13d to rotate about the vertical axis and the horizontal axis, respectively. The drive portion 51 drives the measurement head 3 and the mounting portion 11 in accordance with the instruction from the control portion 50 including the drive control portion 50b.

The position detection portion 52 includes a detection portion for detecting the horizontal and vertical positions of the measurement head 3 relative to the base 2, the vertical rotational position detector 36, and a horizontal rotational position detector 44. The drive mechanism/drive circuit 8 includes the detection portion. The vertical rotary drive 32 includes the vertical rotational position detector 36, and the horizontal rotary drive 40 includes a horizontal rotational position detector 44. The position detection portion 52 outputs the detection results from the detection portion and the detectors to the drive control portion 50b of the control portion 50.

The measurement portion 53 includes the optical system 6 disposed within the measurement head. Based on the instruction from the control portion 50, the measurement portion 53 observes and examines the subject eye image of the subject located in front of the ophthalmologic apparatus 1.

The operation portion 54 includes a touch panel (now shown) disposed on the display surface 25 of the monitor 10. The operation portion 54 receives an operation input to the various operation button images displayed on the display surface 25 and outputs an operation input signal to the control portion 50. Note that in the case wherein the base 2 of the ophthalmologic apparatus 1 includes a joystick and/or operation buttons, the joystick and/or the operation buttons are included in the operation portion 54.

The display portion 55 includes the monitor 10, and displays images, for example, as shown in FIG. 16 on the display surface 25 in accordance with a display control signal from the control portion 50.

The storage portion 56 temporarily stores various data which are used during the control of the ophthalmologic apparatus 1 by the control portion 50. Further, the storage portion 56 stores the examiner data 56a with regard to the rotational position of the supporting arm 13d about the vertical axis and the horizontal axis. The examiner data 56a is predetermined to correspond to information identifying at least one of the examiner or the subject.

The storage portion 56 may store data created by another information processing apparatus or the like as the examiner data 56a. However, in the ophthalmologic apparatus 1 according to the embodiment of the present disclosure, the examiner data 56a is created by a teaching operation, which will be described later, to correspond to at least one of the examiner or the subject. Specifically, the examiner data 56a is the rotational position of the supporting arm 13d about the vertical axis and the horizontal axis detected by the position detection portion 52 when at least one of the examiner or the subject in relation to the ophthalmologic apparatus 1 rotates the supporting arm 13d about the vertical axis and the horizontal axis.

The input portion 57 includes the touch panel (now shown) in the display surface 25 of the monitor 10, more specifically the ID button B1. The input portion 57 receives an input regarding the ID which is information identifying at least one of the examiner or the subject. Note that in the case where the base 2 of the ophthalmologic apparatus 1 includes a numeric keypad for inputting the ID, and in the case where a reader is disposed to read a bar code on an ID card such as a patient ID card or a patient registration card, magnetic data, and the like, the numeric keypad and the reader are included in the input portion 57.

Now, the teaching operation of the ophthalmologic apparatus 1 according to the embodiment of the present disclosure will be described with reference to the flowchart shown in FIG. 12.

Figure 12:
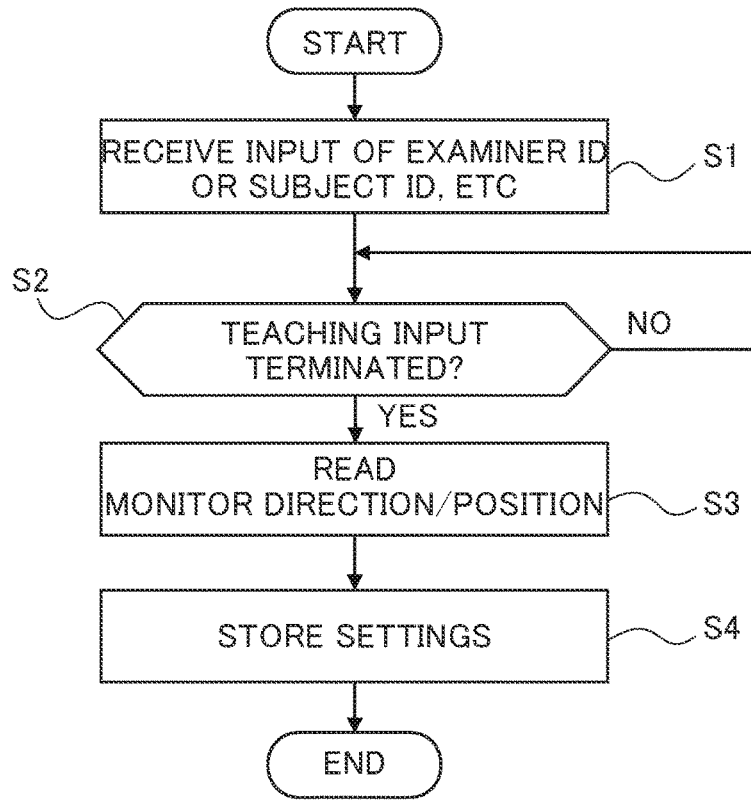
FIG. 12 is a flowchart showing a teaching operation of the ophthalmologic apparatus according to the embodiment of the present disclosure.

The teaching operation shown in the flowchart of FIG. 12 is performed when the examiner data 56a corresponding to the target examiner or subject have not yet created (or have not been stored in the storage portion 56) or when the existing examiner data 56a are updated.

First, in Step S1, the ID of the examiner or the subject whose examiner data 56a will be created is input via the input portion 57. The ID received by the input portion 57 is temporality stored in the storage portion 56.

Next, in Step S2, the program waits for the termination of the teaching operation by the examiner or the subject whose examiner data 56a will be created, and proceeds to Step S3 when the teaching operation is terminated (YES in Step S2). For example, the termination instruction of the teaching operation may be provided when the display surface 25 of the display portion 55 displays a termination instruction button, and the input portion 57 receives an input by the termination instruction button being pressed.

Figure 13:
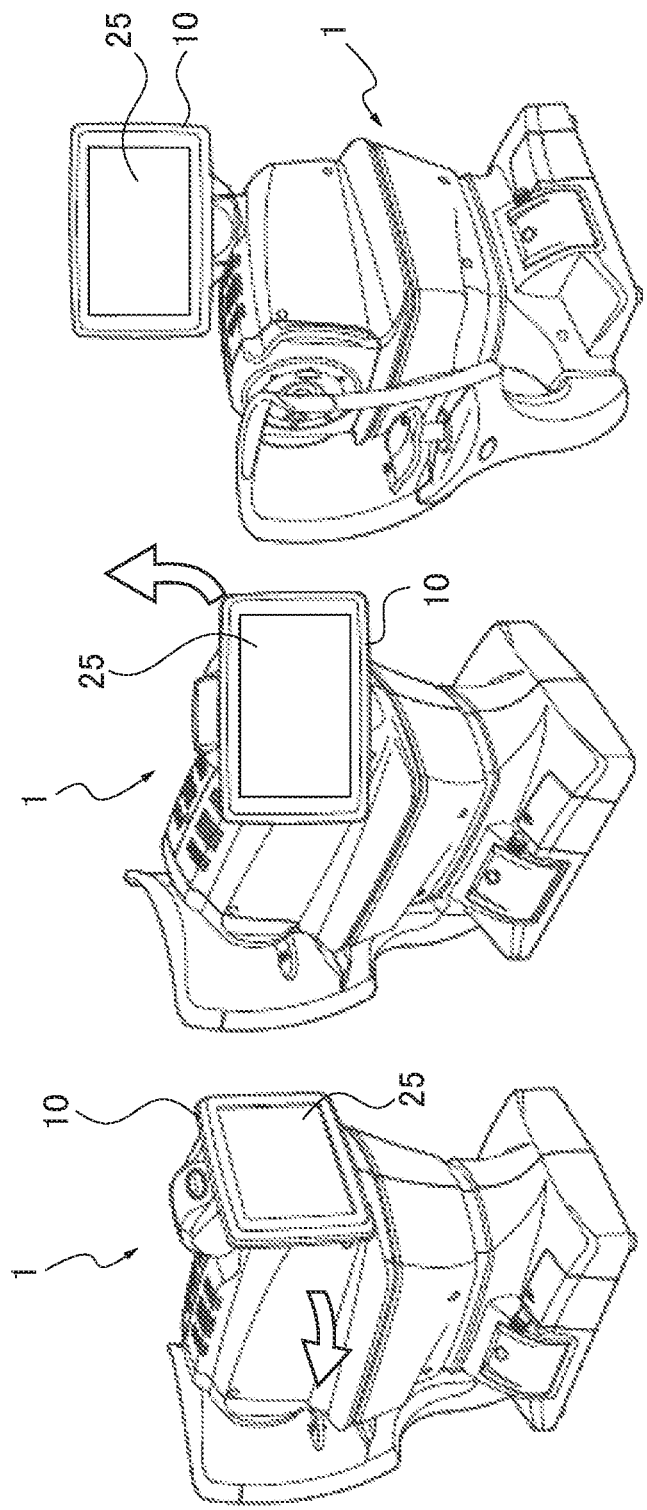
FIG. 13 is a view illustrating the teaching operation of the ophthalmologic apparatus according to the embodiment of the present disclosure.

As shown in FIG. 13, the teaching operation is performed, for example, by moving, turning or rotating the display surface 25 of the monitor 10 in the ophthalmologic apparatus 1 as shown with an arrow in the figure to a desired (preferred) position.

In Step S3, the drive control portion 50b detects the direction of the display surface 25 and the position of the monitor 10 based on the detection result of the position detection portion 52 including the vertical rotational position detector 36 and the horizontal rotational position detector 44.

In Step S4, the direction of the display surface 25 and the position of the monitor 10 detected in Step S3 are linked to the ID of the examiner or the subject input in Step S1 as the rotational position of the supporting arm 13d about the vertical axis and the horizontal axis, and stored in the storage portion 56 as the examiner data 56a.

Now, the operation of the ophthalmologic apparatus 1 according to the embodiment of the present disclosure will be described with reference to the flowchart shown in FIG. 14.

Figure 14:
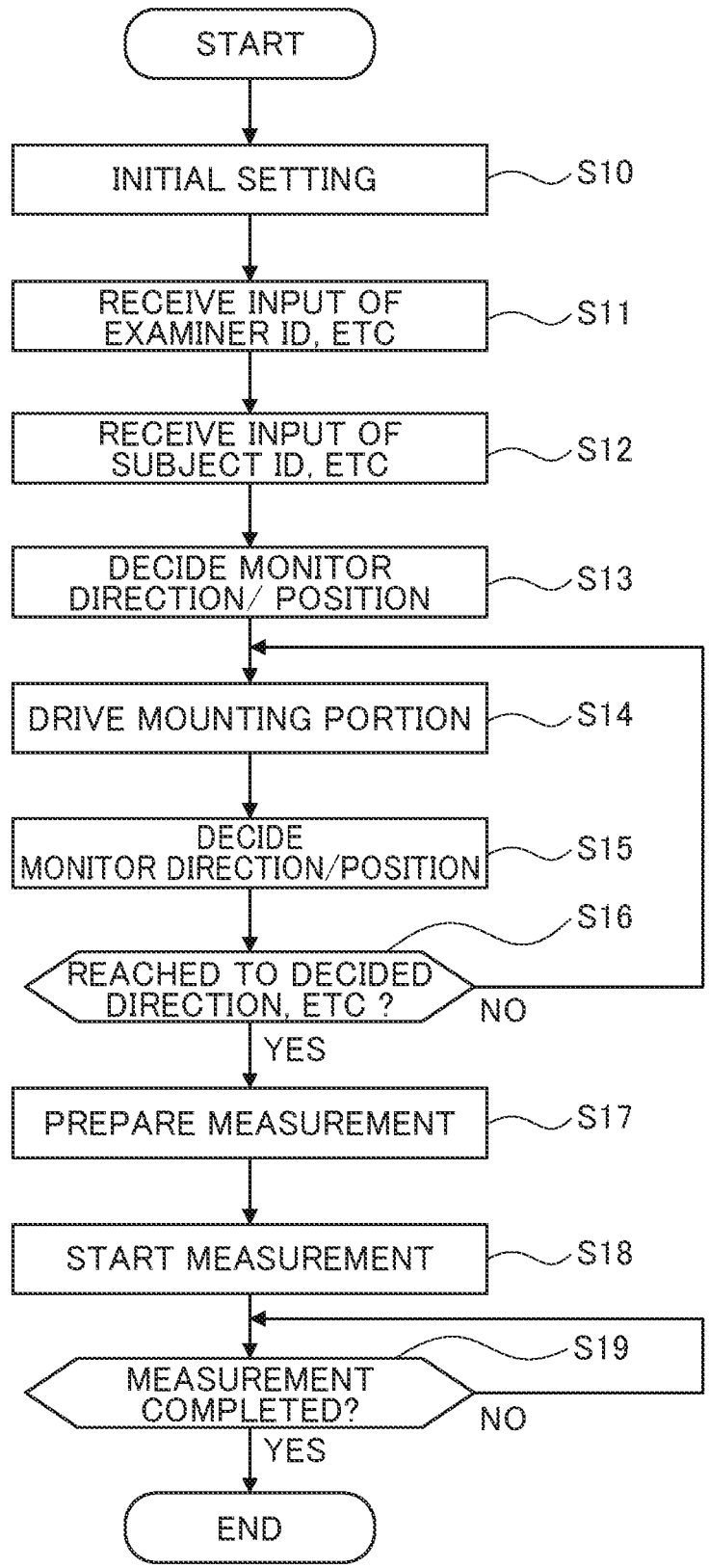
FIG. 14 is a flowchart showing the operation of the ophthalmologic apparatus according to the embodiment of the present disclosure.

The flowchart shown in FIG. 14 is started by turning on the power of the ophthalmologic apparatus 1. First, in Step S10, the program stored in the internal memory 50a of the control portion 50 is executed and the control portion 50 performs an initial setting for each of the portions.

Next, in Step S11, the ID of the examiner in relation to the ophthalmologic apparatus 1 is input via the input portion 57. Similarly, in Step S12, the ID of the subject in relation to the ophthalmologic apparatus 1 is input via the input portion 57. The IDs received by the input portion 57 are temporally stored in the storage portion 56.

Then, in Step S13, the drive control portion 50b reads out the examiner data 56a stored in the storage portion 56 by using the examiner ID or the subject ID input in Step S11 and S12 as a key, and decides the direction of the display surface 25 in the monitor 10 and the position of the monitor 10 corresponding to the ID.

The relation between the direction of the examiner and the direction of the examiner's face relative to the ophthalmologic apparatus 1, and the direction of the display surface 25 and the position of the monitor 10 may be selected as desired. For example, relations as shown in FIGS. 15A to 15D may be available.

As shown in FIG. 15A, when the subject is seated in front of the ophthalmologic apparatus 1 and the examiner stands on the right side of the ophthalmologic apparatus 1, the display surface 25 of the monitor 10 is set to face the right side of the ophthalmologic apparatus 1 as shown in FIG. 15A and FIGS. 3A, 3B.

As shown in FIG. 15B, when the subject is seated in front of the ophthalmologic apparatus 1 and the examiner stands on the back side of the subject, the display surface 25 of the monitor 10 is set to face the front side of the ophthalmologic apparatus 1 as shown in FIG. 15B and FIGS. 2A, 2B.

As shown in FIG. 15C, when the subject is seated in front of the ophthalmologic apparatus 1 and the examiner stands on the right rear side of the ophthalmologic apparatus 1, the display surface 25 of the monitor 10 is set to face the right rear side of the ophthalmologic apparatus 1 as shown in FIG. 15C. Particularly, the display surface 25 of the monitor 10 is set to face slightly upward (see FIGS. 4A, 4B, 5A and 5B) since the examiner is in the standing position.

As shown in FIG. 15D, when the subject is seated in front of the ophthalmologic apparatus 1 and the examiner is also seated behind the ophthalmologic apparatus 1, the display surface 25 of the monitor 10 is set to face the back side of the ophthalmologic apparatus 1 as shown in FIG. 15D and FIGS. 1A, 1B.

Now returning to FIG. 14, in Step S14, the drive control portion 50b drives the mounting portion 11 by using the drive portion 51 including the vertical rotary drive 32 and the horizontal rotary drive 40 toward the direction of the display surface 25 and the position of the monitor 10 decided in Step S13.

In Step S15, the drive control portion 50b detects the direction of the display surface 25 and the position of the monitor 10 based on the detection result of the position detection portion 52 including the vertical rotational position detector 36 and the horizontal rotational position detector 44.

In Step S16, the drive control portion 50b determines whether the display surface 25 and the monitor 10 have reached the direction of the display surface 25 and the position of the monitor 10 decided in Step S13 based on the direction of the display surface 25 and the position of the monitor 10 detected in Step S15. When the drive control portion 50b determines that the display surface 25 and the monitor 10 have reached the decided direction and position (i.e. YES in Step S16), the program proceeds to Step S17. On the other hand, when the drive control portion 50b determines that the display surface 25 and the monitor 10 have not reached the decided direction and position (i.e. NO in Step S16), the program returns to Step S14 and continues driving the mounting portion 11.

In Step S17, the control portion 50 prepares various measurements by the measurement portion 53. In Step S18, the control portion 50 starts the measurements by the measurement portion 53. In Step S19, the operation in the flowchart of FIG. 14 is terminated when the measurements are completed.

In the ophthalmologic apparatus 1 according to the embodiment of the present disclosure as configured above, the drive control portion 50b selects the examiner data 56a stored in the storage portion 56 based on the information received by the input portion 57, and controls the drive portion 51 based on the detection result of the position detection portion 52 and the examiner data 56a such that the rotational position of the supporting arm 13d about the vertical axis and the horizontal axis coincides with the predetermined rotational position.

When the information is input via the input portion 57, the drive control portion 50b controls the drive portion 51 such that the rotational position of the supporting arm 13d about the vertical axis and the horizontal axis coincides with the predetermined rotational position. Accordingly, the examiner does not need to manually adjust the position of the monitor 10 and/or the direction of the display surface 25, and the drive control portion 50b can control to adjust the position of the monitor 10 and the direction of the display surface 25. As a result, it is possible to simplify the operation to adjust the direction and/or the position of the display surface 25 in the monitor 10.

When at least one of the examiner or the subject in relation to the ophthalmologic apparatus 1 rotates the supporting arm 13d about the vertical axis and the horizontal axis, the examiner data 56a stored in the storage portion 56 corresponds to the rotational position of the supporting arm 13d about the vertical axis and the horizontal axis detected by the position detection portion 52. Therefore, the examiner data 56a can be created by at least one of the examiner or the subject rotating or moving the monitor 10. As a result, at least one of the examiner or the subject can adjust the position and/or direction of the display surface 25 in the monitor 10 to his or her preferred position and/or direction with a simple operation.

The embodiment of the present disclosure has been described in detail with reference to the drawings. However, the specific configurations are not limited to the above described embodiment or example, and design changes that do not depart from the gist of the present disclosure are included in the present disclosure.

As an example, in the case where the relative positional relation between the examiner and the ophthalmologic apparatus 1 is limited depending on the installation location of the ophthalmologic apparatus 1 (in the case where the ophthalmologic apparatus 1 is installed along a wall, it is difficult for the examiner to examine the subject along the wall, for example), the examiner data 56a may be updated to set the position of the monitor 10 and the direction of the display surface 25 so as to fit the installation location of the ophthalmologic apparatus 1 every time the ophthalmologic apparatus 1 is placed on a different installation location.

The term "the installation location" used in the specification is a planar position of an examination room or the like where the ophthalmologic apparatus 1 is installed. In addition, the examiner data 56a updated every time the ophthalmologic apparatus 1 is placed on a different installation location is date with regard to the rotational position of the supporting arm 13d about the vertical axis and the horizontal axis predetermined to correspond to information identifying the examiner, the subject and the installation location, and conceptually is data assigned to each point of three-dimensional coordinates determined by the examiner, the subject and the installation location. Note that the examiner data 56a may include features of each installation location (there is no left side, for example) in addition to the data with regard to the rotational position.

Further, an authentication portion may be provided. The authentication portion detects that at least one of the examiner or the subject in relation to the ophthalmologic apparatus 1 approaches the ophthalmologic apparatus 1 and then authenticates the at least one of the examiner or the subject to output information with regard to the at least one of the examiner or the subject. The drive control portion 50b may select the examiner data 56a stored in the storage portion 56 based on the information output from the authentication portion, and control the drive portion 51 based on the detection result of the position detection portion 52 and the examiner data 56a such that the rotational position of the supporting arm 13d about the vertical axis and the horizontal axis coincides with the predetermined rotational position.

As an example of such an authentication portion, it is suitable to use a sensor that detects radio waves, sound waves (including ultrasonic waves), and light (including infrared light) radiated from a probe or terminal the examiner or the subject always have.

Particularly, such probes include those that radiate radio waves or the like according to a specific communication method such as Bluetooth (registered trademark), wireless LAN, or IrDA, for example. In this case, a human sensor 31 may communicate with each of the probes to detect and authenticate each of probes and accordingly each of the examiners or the subjects.

Specifically, the probe of each examiner outputs an ID specific to the each examiner, and the examiner data 56a of the storage portion 56 stores IDs corresponding to the examiners. The examiner can be authenticated when the output ID coincides with the stored ID.

Further, in the ophthalmologic apparatus 1 according to the above embodiment, the ID of at least one of the examiner or the subject is input via the touch panel of the monitor 10. However, the input of the ID by the input portion 57 is not limited to that described above, and the ID may be suitably input in a various way.

The number of the examiner IDs may be less than that of the subject (patient) IDs. Accordingly, a list of the examiner IDs which have already registered is displayed in a pull-down menu when the examiner touches the examiner ID display area 25k of the display surface 25, and then the examiner touches one of the IDs to select his or her ID, for example.

Figure 17:
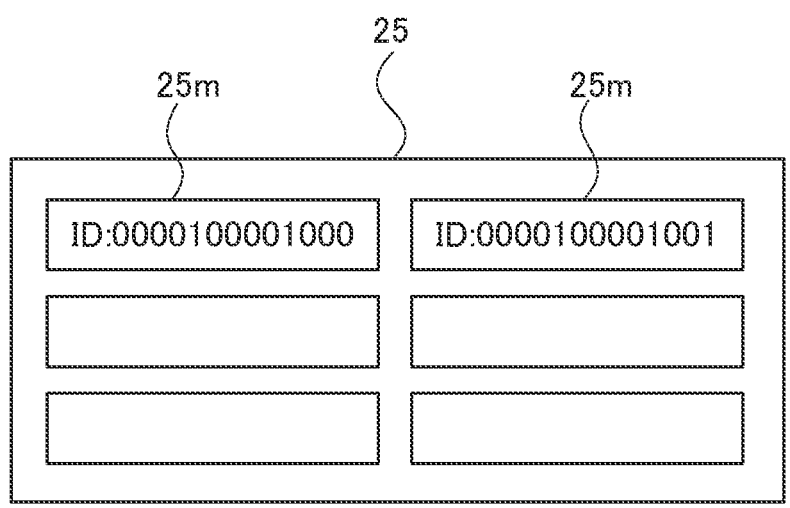
FIG. 17 is a view illustrating an example of images on the display surface when starting up the ophthalmologic apparatus according to the embodiment of the present disclosure.

Alternatively, as shown in FIG. 17, the display surface 25 may display icons 25m indicating the examiner IDs which have already registered when starting the ophthalmologic apparatus 1, and the examiner may touch one of the icons 25m corresponding to his or her ID to select his or her ID.

In addition, each of the examiner IDs and the subject IDs may be preset either to perform the driving operation of the mounting portion 11 or not to perform the driving operation of the mounting portion 11.

Further, the configuration of the support member which supports the monitor to rotate about the vertical axis and the horizontal axis is not limited to the above embodiment. Various configurations may be adopted as long as the monitor is supported to rotate about the vertical axis and the horizontal axis. As an example of the support member which supports the monitor to rotate about the vertical axis and the horizontal axis, a configuration which supports the display surface of the monitor to move in a substantially vertical direction and supports the monitor to rotate about the vertical axis may be adopted. Moreover, in another configuration which may be effectively adopted, the monitor may be attached to the support member to rotate about the horizontal axis and the upper portion of the measurement head or the support member may be supported relative to a body of the measurement head to rotate about the vertical axis. In addition, the support member and the monitor may be configured to be detachable relative to the body of the measurement head.

What is claimed is:

1. An ophthalmologic apparatus comprising
a base;
a measurement head supported by the base to move in a horizontal direction and a vertical direction perpendicular to the horizontal direction while facing a subject in front of the base, the measurement head being configured to observe and examine a subject eye image via an optical system;
a monitor comprising a display surface configured to display at least the subject eye image and an operation button image;
a mounting portion disposed in an upper portion of the measurement head and comprising a support portion configured to rotatably support the monitor about a vertical axis and a horizontal axis relative to the measurement head, the monitor being attached to the mounting portion;
a drive portion configured to rotate the support portion and the monitor supported by the support portion about the vertical axis and the horizontal axis relative to the measurement head;
a detection portion configured to detect a rotational position of the support portion about the vertical axis and the horizontal axis;
an input portion configured to receive an input with regard to information that identifies at least one of an examiner and the subject;
a storage portion configured to store data with regard to the rotational position of the support portion about the vertical axis and the horizontal axis, the data being predetermined to correspond to the information; and
a drive control portion configured to select the data stored in the storage portion based on the information received by the input portion, and to control the drive portion based on the selected data and a detection result of the detection portion so that the rotational positions of the support portion and the monitor supported by the support portion about the vertical axis and the horizontal axis are rotated to coincide with a predetermined rotational position,
wherein the predetermined rotational position of the support portion and the monitor supported by the support portion comprises:
a first position in which the monitor faces forward of the ophthalmologic apparatus and a second position in which the monitor faces rearward of the ophthalmologic apparatus, the first and second position being set by a rotation of the support portion about the horizontal axis; and
a third position in which the monitor faces rightward of the ophthalmologic apparatus and a fourth position in which the monitor faces leftward of the ophthalmologic apparatus, the third and fourth positions being set by a rotation of the support portion about the vertical axis.

2. The ophthalmologic apparatus according to claim 1, wherein the data is a rotational position of the support portion about the vertical axis and the horizontal axis detected by the detection portion when at least one of the examiner and the subject in relation to the ophthalmologic apparatus rotates the support portion about the vertical axis and the horizontal axis.

3. The ophthalmologic apparatus according to claim 2, wherein the data is updated every time the ophthalmologic apparatus is placed on a different installation location.

4. The ophthalmologic apparatus according to claim 2, wherein the data is updated by data with regard to the rotational position of the support portion about the vertical axis and the horizontal axis detected by the detection portion in a condition where the drive portion is controlled by the drive control portion.

5. The ophthalmologic apparatus according to claim 3, wherein the data is updated by data with regard to the rotational position of the support portion about the vertical axis and the horizontal axis detected by the detection portion in a condition where the drive portion is controlled by the drive control portion.

6. The ophthalmologic apparatus according to claim 1, further comprising an authentication portion configured to detect that at least one of the examiner and the subject approaches the ophthalmologic apparatus and then to authenticate the at least one of the examiner and the subject to output information with regard to the at least one of the examiner and the subject, and wherein the drive control portion is configured to select data stored in the storage portion based on the information output from the authentication portion, and to control the drive portion based on the selected data and a detection result of the detection portion so that the rotational positions of the support portion and the monitor supported by the support portion about the vertical axis and the horizontal axis are rotated to coincide with the predetermined rotational position.

7. The ophthalmologic apparatus according to claim 1, wherein the data is updated by data with regard to the rotational position of the support portion about the vertical axis and the horizontal axis detected by the detection portion in a condition where the drive portion is controlled by the drive control portion.

* * * * *